United States Patent
Coulter

(10) Patent No.: US 8,951,570 B2
(45) Date of Patent: Feb. 10, 2015

(54) MANUFACTURE OF MULTIPLE MINICAPSULES

(75) Inventor: Ivan Coulter, Dublin (IE)

(73) Assignee: Sigmoid Pharma Limited, Dublin (IE)

(*) Notice: Subject to any disclaimer, the term of this patent is extended or adjusted under 35 U.S.C. 154(b) by 355 days.

(21) Appl. No.: 12/597,154

(22) PCT Filed: Apr. 25, 2008

(86) PCT No.: PCT/IE2008/000048
§ 371 (c)(1),
(2), (4) Date: Nov. 16, 2010

(87) PCT Pub. No.: WO2008/132707
PCT Pub. Date: Nov. 6, 2008

(65) Prior Publication Data
US 2011/0052645 A1    Mar. 3, 2011

Related U.S. Application Data

(60) Provisional application No. 60/924,007, filed on Apr. 26, 2007.

(51) Int. Cl.
| | | |
|---|---|---|
| A61K 9/50 | (2006.01) |
| A61K 9/14 | (2006.01) |
| B29B 9/00 | (2006.01) |
| B32B 5/16 | (2006.01) |
| A61K 47/00 | (2006.01) |
| B01J 13/04 | (2006.01) |
| A61K 9/16 | (2006.01) |

(52) U.S. Cl.
CPC ............ *B01J 13/04* (2013.01); *A61K 9/1617* (2013.01); *A61K 9/1635* (2013.01); *A61K 9/1652* (2013.01); *A61K 9/1658* (2013.01); *A61K 9/167* (2013.01); *A61K 9/1694* (2013.01); *A61K 9/5026* (2013.01); *A61K 9/5036* (2013.01); *A61K 9/5057* (2013.01); *A61K 9/5089* (2013.01)
USPC ............ 424/499; 424/489; 264/13; 428/402; 428/403; 428/402.2; 428/402.24; 514/774

(58) Field of Classification Search
None
See application file for complete search history.

(56) References Cited

U.S. PATENT DOCUMENTS

| | | |
|---|---|---|
| 4,279,632 A | 7/1981 | Frosch et al. |
| 4,379,454 A | 4/1983 | Campbell et al. |
| 4,422,985 A | 12/1983 | Morishita et al. |

(Continued)

FOREIGN PATENT DOCUMENTS

| | | |
|---|---|---|
| AU | 1977031116 | 12/1976 |
| AU | 627220 B2 | 8/1992 |

(Continued)

OTHER PUBLICATIONS

Chourasia et al., "Pharmaceutical approaches to colon targeted drug delivery systems," *J. Pharm. Pharmaceut. Sci.* 6(1):33-66-2003.

(Continued)

*Primary Examiner* — Jeffrey T Palenik
(74) *Attorney, Agent, or Firm* — Klarquist Sparkman, LLP

(57) ABSTRACT

An extrusion process comprises extruding a material that is flowable when heated and passing the extrudate thus formed through a nozzle 10 to shape the extrudate into a plurality of substantially uniformly shaped elements such as minispheres or minicapsules.

38 Claims, 9 Drawing Sheets

(56) References Cited

U.S. PATENT DOCUMENTS

| | | | |
|---|---|---|---|
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,362,564 A | 11/1994 | Suzuki et al. |
| 5,385,737 A | 1/1995 | Shigeno et al. |
| 5,418,010 A * | 5/1995 | Janda et al. ............. 427/213.31 |
| 5,478,508 A | 12/1995 | Suzuki et al. |
| 5,480,655 A | 1/1996 | Jizomoto et al. |
| 5,492,701 A | 2/1996 | Cervos et al. |
| 5,500,224 A | 3/1996 | Vranckx et al. |
| 5,510,118 A | 4/1996 | Bosch et al. |
| 5,529,783 A | 6/1996 | Burke et al. |
| 5,571,533 A | 11/1996 | Santus et al. |
| 5,645,856 A | 7/1997 | Lacy et al. |
| 5,650,232 A | 7/1997 | Glenn et al. |
| 5,665,386 A | 9/1997 | Benet et al. |
| 5,795,590 A | 8/1998 | Kiefer et al. |
| 5,827,531 A | 10/1998 | Morrison et al. |
| 5,871,774 A | 2/1999 | Lemelson |
| 5,882,680 A | 3/1999 | Suzuki et al. |
| 6,022,562 A | 2/2000 | Autant et al. |
| 6,113,936 A | 9/2000 | Takebayashi et al. |
| 6,146,663 A | 11/2000 | Bissery et al. |
| 6,174,466 B1 | 1/2001 | Kiefer et al. |
| 6,190,692 B1 | 2/2001 | Busetti et al. |
| 6,251,661 B1 | 6/2001 | Urabe et al. |
| 6,267,985 B1 | 7/2001 | Chen et al. |
| 6,284,271 B1 | 9/2001 | Lundberg et al. |
| 6,309,663 B1 | 10/2001 | Patel et al. |
| 6,361,298 B1 | 3/2002 | Kiefer et al. |
| 6,429,089 B1 | 8/2002 | Matsuki |
| 6,457,339 B2 | 10/2002 | Komura |
| 6,531,150 B1 | 3/2003 | Sunohara et al. |
| 6,569,463 B2 | 5/2003 | Patel et al. |
| 6,585,997 B2 | 7/2003 | Moro et al. |
| 6,761,903 B2 | 7/2004 | Chen et al. |
| 6,923,988 B2 | 8/2005 | Patel et al. |
| 6,972,132 B1 | 12/2005 | Kudo et al. |
| 7,267,813 B2 | 9/2007 | Watanabe et al. |
| 7,374,779 B2 | 5/2008 | Chen et al. |
| 2001/0003589 A1 | 6/2001 | Neuer et al. |
| 2001/0024658 A1 | 9/2001 | Chen et al. |
| 2002/0009457 A1 | 1/2002 | Bowersock et al. |
| 2002/0098242 A1 | 7/2002 | Darder |
| 2003/0045516 A1 | 3/2003 | Luly et al. |
| 2003/0078194 A1 | 4/2003 | Cho et al. |
| 2003/0104048 A1 | 6/2003 | Patel et al. |
| 2003/0124061 A1 | 7/2003 | Roberts |
| 2003/0180352 A1 | 9/2003 | Patel et al. |
| 2003/0193102 A1 | 10/2003 | Yan |
| 2003/0232076 A1 | 12/2003 | Makino et al. |
| 2003/0235595 A1 | 12/2003 | Chen et al. |
| 2004/0028619 A1 | 2/2004 | Watanabe et al. |
| 2004/0029855 A1 | 2/2004 | Klaveness et al. |
| 2004/0062802 A1 | 4/2004 | Hermelin |
| 2004/0126428 A1 | 7/2004 | Hughes et al. |
| 2005/0037077 A1 | 2/2005 | Legrand et al. |
| 2005/0095288 A1 | 5/2005 | Honea |
| 2005/0249807 A1* | 11/2005 | Brown et al. ............. 424/464 |
| 2006/0018965 A1* | 1/2006 | Moodley et al. ............. 424/470 |
| 2006/0034937 A1 | 2/2006 | Patel |
| 2006/0068019 A1 | 3/2006 | Dalziel et al. |
| 2006/0135441 A1 | 6/2006 | Khodadoust et al. |
| 2006/0222701 A1* | 10/2006 | Kulkarni et al. ............. 424/451 |
| 2007/0292523 A1 | 12/2007 | Moodley et al. |
| 2008/0020018 A1 | 1/2008 | Moodley et al. |
| 2008/0107694 A1 | 5/2008 | Trogden et al. |
| 2008/0113031 A1 | 5/2008 | Moodley et al. |
| 2008/0124279 A1 | 5/2008 | Andremont et al. |
| 2008/0311201 A1 | 12/2008 | Der-Yang et al. |
| 2008/0318912 A1 | 12/2008 | Fox et al. |
| 2010/0136105 A1 | 6/2010 | Chen et al. |
| 2010/0255087 A1 | 10/2010 | Coulter |

FOREIGN PATENT DOCUMENTS

| | | | |
|---|---|---|---|
| CA | 2170748 | 8/1994 | |
| CA | 2376261 | 6/2000 | |
| CN | 1557283 | 12/2004 | |
| DE | 19848849 | 10/1998 | |
| DE | 19848849 | 2/2000 | |
| EP | 0525731 | 2/1993 | |
| EP | 0 550 067 | 7/1993 | |
| EP | 0621775 | 11/1994 | |
| EP | 0650721 | 5/1995 | |
| EP | 0760237 | 3/1997 | |
| EP | 0778083 | 6/1997 | |
| EP | 0922451 | 6/1999 | |
| EP | 0813876 | 3/2002 | |
| EP | 0789561 | 4/2004 | |
| EP | 1811979 | 11/2008 | |
| JP | A-58 013508 | 1/1983 | |
| JP | A-58 077810 | 5/1983 | |
| JP | 59-088420 | 5/1984 | |
| JP | S61126016 A | 6/1986 | |
| JP | A-61 151119 | 7/1986 | |
| JP | 64-000015 | 1/1989 | |
| JP | H0549899 A | 3/1993 | |
| JP | EP 0 595 263 A1 * | 5/1994 | ............. B01J 13/04 |
| JP | H06254382 A | 9/1994 | |
| JP | 7247215 A | 9/1995 | |
| JP | 2000-247911 | 9/2000 | |
| JP | 2000-302654 | 10/2000 | |
| JP | 64 000015 | 8/2010 | |
| WO | WO 93/00063 | 1/1993 | |
| WO | WO 97/02017 | 1/1997 | |
| WO | WO 98/18610 | 5/1998 | |
| WO | WO 98/50018 | 11/1998 | |
| WO | WO 98/50033 | 11/1998 | |
| WO | WO 99/06024 | 2/1999 | |
| WO | WO 99/13914 | 3/1999 | |
| WO | WO 00/33862 | 6/2000 | |
| WO | WO 00/69420 | 11/2000 | |
| WO | WO 01/08666 | 2/2001 | |
| WO | WO 01/37808 | 5/2001 | |
| WO | WO 01/51008 | 7/2001 | |
| WO | WO 01/80831 | 11/2001 | |
| WO | WO 03/018134 | 3/2003 | |
| WO | WO 03/020243 | 3/2003 | |
| WO | WO 03/056938 | 7/2003 | |
| WO | WO 03/092741 | 11/2003 | |
| WO | WO 2004/022220 | 3/2004 | |
| WO | WO 2004/064997 | 8/2004 | |
| WO | WO 2004/084870 | 10/2004 | |
| WO | WO 2005/020994 | 3/2005 | |
| WO | WO 2005/030205 | 4/2005 | |
| WO | WO 2005/048998 | 6/2005 | |
| WO | WO 2005/072088 | 8/2005 | |
| WO | WO 2005/074913 | 8/2005 | |
| WO | WO 2005/100454 | 10/2005 | |
| WO | WO 2006/026592 | 3/2006 | |
| WO | WO 2006/035416 | 4/2006 | |
| WO | WO 2007/014445 | 2/2007 | |
| WO | WO 2007/018943 | 2/2007 | |

OTHER PUBLICATIONS

Final Office Action dated Jun. 17, 2011, from U.S. Appl. No. 11/663,834 filed Mar. 27, 2007.
Non-Final Office Action dated Jul. 15, 2011, from U.S. Appl. No. 11/236,549, filed Sep. 28, 2005.
Cannon, "Oral Solid Dosage Forms of Lipid-based Drug Delivery Systems," *AM Pharm Rev* 8(1):108-115, 2005.

(56) References Cited

OTHER PUBLICATIONS

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.
Al-Meshal et al., "Oral administration of liposomes containing cyclosporine: a pharmacokinetic study," *International Journal of Pharmaceutics* 168:163-168, 1998.
Anderberg et al., "Sodium Caprate Elicits Dilatations in Human Intestinal Tight Junctions and Enhances Drug Absorption by the Paracellular Route," *Pharmaceutical Research* 10(6):857-864, 1993.
Barnes et al., "Theophylline: New Perspectives for an Old Drug," *AM J Respir Crit Care Med* 167:813-818, 2003.
Borel et al., "Carotenoids in biological emulsions: solubility, surface-to-core distribution, and release from lipid droplets," *Journal of Lipid Research* 37:250-261, 1996.
Chowdary et al., "Controlled Nifedipine Release from Microcapsules of its Dispersions in PVP-MCC and HPC-MCC," *Drug Development and Industrial Pharmacy* 21(10):1183-1192, 1995.
Drewe et al., "The absorption site of cyclosporine in the human gastro-intestinal tract," *Br. J clin. Pharmac.* 33:39-43, 1992.
Gursoy et al., "Self-emulsifying drug delivery systems (SEDDS) for improved oral delivery of lipophilic drugs," *Biomedicine & Pharmacotherapy* 58:173-182, 2004.
Ikegawa et al., Inhibition of P-glycoprotein by flavonoid derivatives in Adriamycin-resistant human myelogenous leukemia (K562/ADM)cells, *Cancer Letters* 177:89-93, 2002.
Manakova et al., "Failure of FK506 (tacrolimus) to alleviate apomorphine-induced circling in rat Parkinson model in spite of some cytoprotective effects in SH-SY5Y dopaminergic cells," *Brain Research* 1038:83-91, 2005.
McGinity et al., Aqueous Polymeric Coatings for Pharmaceuticals Dosage Forms, *Marcel Dekker, Inc.*, 1997.
Miller et al., "Controlled Trial of Nimodipine in Amyotrophic Lateral Sclerosis," *Neuromusc. Disord.*, 6(2):101-104, 1996.
Ribeiro et al., "Microencapsulation of lipophilic drugs in chitosan-coated alginate microspheres," *International Journal of Pharmaceutics* 187:115-123, 1999.
Strowig et al., Comparison of Insulin Monotherapy and Combination Therapy with Insulin and Metformin or Insulin and Troglitazone in Type 2 Diabetes, *Diabetes Care* 25(10):1691-1698, 2002.
Sweetman and Martindale, "Nimodipine," *Cardiovascular Drugs* p. 946, 2002.
Yang et al., "Transport and uptake characteristics of a new derivative of berberine (CPU-86017) by human intestinal epithelial cell line: Caco-2," *Acta Pharmacol Sin* 24(12):1185-1191, 2003.
Yeh et al., "Effect of Medium-Chain Glycerides on Physiological Properties of Rabbit Intestinal Epithelium in Vitro," *Pharmaceutical Research* 11(8):1148-1154, 1994.
Zhang et al., "P-glycoprotein restricted transport of nimodipine across blood-brain barrier," *Acta Pharmacol Sin* 24(9):903-906, 2003.
Zuber et al., "Reversible cerebral angiopathy," *J. Neurol* 253:1585-1588, 2006.
Non-Final Office Action from U.S. Appl. No. 11/236,549 dated May 5, 2009.
Non-Final Office Action from U.S. Appl. No. 11/236,549 dated Oct. 6, 2010.
Non-Final Office Action from U.S. Appl. No. 11/663,834 dated Mar. 3, 2010.
Madene et al., "Flavour encapsulation and controlled release—a review," *International Journal of Food Science and Technology* 41:1-21, 2006.
Non-Final Office Action from co-pending U.S. Appl. No. 12/594,542 dated Oct. 5, 2012.
Final Office Action from co-pending U.S. Appl. No. 12/594,553 dated Sep. 10, 2012.
Non-Final Office Action from co-pending U.S. Appl. No. 13/321,149 dated Nov. 9, 2012.
Non-Final Office Action from co-pending U.S. Appl. No. 13/441,780 dated Nov. 28, 2012.
Milojevic et al., "Amylose as a coating for drug delivery to the colon: Preparation and in vitro evaluation using 5-aminosalicylic acid pellets," *Journal of Controlled Release* 38:75-84, 1996.
Murthy et al., "Treatment of Dextran Sulfate Sodium-Induced Murine Colitis by Intracolonic Cyclosporin," *Digestive Diseases and Sciences* 38(9):1722-1734, Sep. 1993.
NIMOTOP FDA approved labeling text, Dec. 2005.
Non-final Office action from U.S. Appl. No. 12/594,534, dated Mar. 30, 2012, 31pp.
Non-final Office action from U.S. Appl. No. 12/598,395, dated Mar. 26, 2012, 11pp.
Final Office action from U.S. Appl. No. 11/236,549, dated Mar. 15, 2012, 25pp.
Extended European Search Report for corresponding European Application No. 12173377.8 dated Apr. 4, 2013.
Rodriguez et al. "Colonic budesonide delivery from ph-dependent microcapsules containing lipidic cores," *Acta Technologiae et Legis Medicamenti*, XI(1):45-52, 2000.
Dhara et al., "Stability of Sodium Dodecyl Sulfate Micelles in the Presence of a Range of Water-Soluble Polymers: A Pressure-Jump Study," *J. Phys. Chem. B.*, 105: 7133-7138; 2001.
Greener et al., "Interaction of Anionic Surfactants with Gelatin: Viscosity Effects," *Macromolecules*, 20: 2490-2498; 1987.
Holmberg et al., *Surfactants and Polymers in Aqueous Solution*. John Wiley & Sons, Ltd. 2002.
Muller et al. "Competitive Adssorption of Gelatin and Sodium Dodecylbenzenesulfonate at Hydrophobic Surfaces," *Langmuir*, 14: 3107-3114; 1998.
Wesley et al., "Structure of Polymer/Surfactant Complexes Formed by Poly(2-(dimethylamino)ethyl metharylate) and Sodium Dodecyl Sulfate," *Langmuir* 18: 5704-5707; 2002.
Shioji, Yusaku "Manufacturing technology of solid formulation", CMC Publishing Co. Ltd., pp. 46-48 and 174-177, Jan. 27, 2003.
Office action issued for Japanese Patent Application No. 2006-507572.

\* cited by examiner

MANUFACTURE OF MULTIPLE MINICAPSULES

CROSS REFERENCE TO RELATED APPLICATIONS

This is the U.S. National Stage of International Application No. PCT/IE2008/000048, filed Apr. 25, 2008, which was published in English under PCT Article 21(2), which in turn claims the benefit of U.S. Provisional Application No. 60/924,007, filed Apr. 26, 2007. The provisional application is incorporated herein in its entirety.

The present invention relates to the manufacture of multiple minicapsules or minispheres, containing a pharmaceutical entity.

DESCRIPTION OF PRIOR ART

A number of formulation approaches has been developed to enhance the solubility, permeability and/or stability of active pharmaceutical actives or other compounds that may otherwise have been rendered incompatible with existing drug administration formats. A couple of such approaches include seamless minicapsules and melt extrusion processes that produce a range of drug pellet, pill, capsule or other formats.

A process for manufacturing seamless minicapsules is described in U.S. Pat. No. 5,882,680

The principle of seamless minicapsule formation is the utilisation of surface tension of one or more different solutions which when ejected through an orifice or nozzle with a certain diameter and subject to specific frequencies and gravitational flow, forms into a spherical form and falls into a cooling air flow or into a cooling or hardening solution and the outer shell solution where it is gelled or solidified. This briefly describes the formation of seamless minispheres.

The core solution is mainly a hydrophobic solution or suspension. The outer shell solution is normally gelatin based. However a hydrophilic solution can also be encapsulated with the existence of an intermediate solution, which can avoid the direct contact of the hydrophilic core solution with the outer shell. With a nozzle having a single orifice, a minicapsule or a bead of shell/core mixed suspension can be processed. With the nozzle having two orifices (centre and outer), a hydrophobic solution can be encapsulated. With the nozzle having three or more orifices seamless minicapsules for various applications can be processed.

Nimodipine multiparticulate seamless minicapsules having an average diameter of 1.00-3.00 mm, more especially in the range 1.50-1.80 mm are described in our WO2006/035417A.

The resulting one-, two- or three-layer minicapsules or minispheres may be further processed through coating with various controlled release polymers which modulates the release of active pharmaceutical actives from the underlying minicapsule or minisphere cores, entireties or parts thereof. In accordance with previous inventions the drug loaded minicapsules are coated with the rate-controlling polymers to achieve a target dissolution rate. The drug released from these minicapsules is diffusion controlled as the polymer swells and becomes permeable, it allows for controlled release in the GIT. In order to achieve a suitable dissolution profile, the following parameters require consideration, efficient process/conditions, drug solubility/particle size, minicapsule surface area, minicapsule diameter and coating polymer suitability.

The known minicapsule process has a number of benefits for a range of active pharmaceutical compounds but there are also potential limitations including problems regarding compatibilities of core formulations with the shell material and/or the buffer layer, where required. Another potential limitation is low active pharmaceutical compound payloads leading to large, patient-unfriendly pill sizes. Still another potential limitation is that controlled release is a function of the shell or shell coating and may thus be limiting. Yet another limitation relates to possible incompatibilities between the shell and the core or the buffer layer which may result in incomplete encapsulation or irregular shaped minicapsules.

This invention is directed towards providing an improved minicapsule process which will address at least some of these problems. The improved process may lead to the development of a number of formats to further enhance the controlled release, solubility, permeability, dissolution and stability of a range of active pharmaceutical compounds as well as other entities.

STATEMENTS OF INVENTION

According to the invention there is provided an extrusion process comprising the steps of extruding a material that is flowable when heated and passing the extrudate thus formed through a nozzle to shape the extrudate into a plurality of substantially uniformly shaped elements such as minispheres or minicapsules.

In one embodiment a force is applied to the nozzle as the extrudate is passed through the nozzle. The force may be a vibrational force.

Alternatively or additionally a cutting force is applied to the extrudate. The cutting force may be applied to the extrudate on exiting the nozzle. The cutting force may be applied by one or more selected from a rotary shear force, a flywheel cutter, a fixed blade and a moving blade.

In one case the nozzle has more than one passageway. At least some of the passageways may be concentric.

In one embodiment the nozzle has more than one inlet port, the melt extrudate being delivered into at least one of the inlet ports of the nozzle. In one case another medium is delivered into one of the inlet ports of the nozzle. The media entering different nozzle inlets may be at different temperatures or pressures.

The medium may be an encapsulating medium, a coating, and/or comprise an active ingredient such as a pharmaceutical.

In one embodiment the process comprises the step of cooling the shaped elements. The shaped elements may be cooled in a cooling gas such as air. The shaped elements may be cooled in a cooling liquid.

In one embodiment the material that is extruded contains a pharmaceutical, a biopharmaceutical, and/or a nutritional supplement.

In one embodiment the constituents of the material to be melt extruded are blended and fed through a temperature regulated feeder.

In one case a first medium is delivered to a first inlet of the nozzle from a first extruder and a second medium is delivered to a second inlet of the nozzle from a second extruder.

In one embodiment a first medium is delivered to a first inlet of the nozzle from a first extruder and a second medium is pumped by a pumping means to a second inlet of the nozzle.

The material for melt extrusion may comprise one or more of one or more of active pharmaceutical compounds together with non-therapeutic compounds. The non therapeutic components may be selected from one or more of meltable polymers; plasticisers; solubility enhancers; permeability enhancers; viscosity modifiers; pH modulators; surfactants, hydrogels; ion-exchange resins; and controlled release polymers.

The material may comprise a pharmaceutical in crystalline form, a pharmaceutical in stabilised amorphous form, a pharmaceutical in stabilised micronised form, a pharmaceutical in stabilised nanoformulated form, a non-covalently conjugated pharmaceutical or a covalently conjugated pharmaceutical.

The invention also provides substantially uniformly shaped elements when made by a process of the invention. The elements may be minispheres or minicapsules. The elements may comprise one layer or two or more layers.

In another aspect the invention provides an extrusion apparatus comprising an extruder for melting extruded material, an outlet nozzle into which the melted extrudate is delivered, and means for applying a force so that the material exiting the nozzle is formed into substantially uniformly shaped elements such as minispheres or minicapsules.

In one case the apparatus comprises a vibrator to apply force to the nozzle.

Alternatively or additionally the apparatus comprises cutting means to apply a cutting force. The cutting means may be located adjacent to the nozzle exit. The cutting means may comprise one or more selected from a rotary shear force; a flywheel cutter; a fixed blade; and a moving blade.

In one embodiment the nozzle has a single outlet. The nozzle may comprise at least two outlets. The outlets may comprise an inner outlet and an outer outlet surrounding the inner outlet.

In one case the outlets are concentric.

In one embodiment the nozzle comprises a first inlet into which extrudate from the extruder is delivered and at least one further inlet for delivery of material into the nozzle. The apparatus may comprise pump means for delivery of material through the further nozzle inlet.

In one embodiment the apparatus comprises cooling means for cooling material that exits the nozzle.

The invention also provides single layer melt-extruded minispheres.

The invention further provides a two-layer product comprising a melt-extruded core and an outer layer. In one case the outer layer is a melt-extruded layer.

One aspect of the present invention is a process combining aspects of traditional hot melt extrusion and minicapsule processing technologies to produce (using a combination of meltable extrudable polymers, plasticisers, and/or pharmaceutical compounds) products, of uniform or fairly uniform shape, that exhibit controlled release formulations.

A hot melt extrusion (HME) process is known in the pharmaceutical industry. Building on knowledge from the plastics industry, formulators can extrude combinations of drugs, polymers, plasticisers and other functional excipients into various final forms to achieve desired drug-release profiles. The benefits of using HME over traditional processing techniques include fewer unit operations; better content uniformity; an anhydrous process; a dispersion mechanism for poorly soluble drugs; a low energy alternative to high-shear granulation; less processing time compared with conventional wet granulation. However, one of the problems with known techniques is that the final products are non-uniform in size and or shape. Generally, the end product is cylindrical or rod-like with irregular edges. To overcome the irregularity in shape, the cylindrical or rod-like products are subjected to a spheronisation process to smoothen the rough edges and produce a more spherical shaped end product that may be post-processed more easily. A further problem is that the process often entails high processing and sheer mixing forces that may denature certain drugs and, indeed, polymers.

In traditional melt extrusion processing, the hot extruded mix is passed through a ring nozzle plate and cut to similar sized particles using a rotating knife. In one aspect of the present invention a modified vibrating nozzle is used through which the hot extrudate passes and from which it drops to form seamless spherical spheres. The nozzle may be non-circular to enable the production of single or multiple strip-forms of extrudate with a fairly regular square, rectangular or other shape. The products of the invention are uniform or fairly uniform in size and shape which is due to a combination of the flow rate of molten extrudate through single or concentric nozzles and the vibrational frequency to which the nozzle is subjected to. The spherical nature of the resulting product is due to the surface tension of the extrudate complex. The process involves a gravitational flow of consecutive droplets that are air cooled or cooled in a liquid to produce very regular shaped and size-tunable minispheres or minicapsules.

In one aspect the invention provides a process whereby the seamless minicapsule process is modified to include a melt extrusion feeder whereby the hot extrudate is blended and homogenised and fed through an appropriate vibrational nozzle structure at a suitable temperature to provide appropriate viscosity; at suitable pressure to provide the requisite flow-rate and the nozzle subjected to an appropriate vibrational frequency to result in the desired seamless spherical diameter and form.

The invention provides a process wherein the nozzle is a single nozzle or is comprised of a polycentric nozzle (such as a di-centric, tri-centric or greater) which permit a number of different extrudates to flow through each concentric nozzle. The extrudates in such forms, when single-layer, once cooled, are solid or semi-solid, or when multi-layered, once cooled, may be any of liquid, semi-solid or solid form.

The invention provides a process whereby the resulting minispheres or minicapsules comprise a liquid, solid, or semi-solid core that incorporates controlled release polymers thereby negating the requirement for the application of controlled release polymer coatings. The encapsulating material may comprise, in total or in part, controlled release polymers.

The invention also enables the development of single-, two- or multi-layer minicapsules to be produced with our without the inclusion of a gelling agent, such as gelatin. This can overcome issues associated with inherent incompatibility of a gelling agent, such as gelatine, with various emulsion- or liquid-based drug formulations, such incompatibilities being associated with surface tension or other formulation-based factors. Thus, the process is adapted to the needs of a very wide range of active pharmaceutical compounds.

The inclusion of a gelling agent, with or without other melt extrudible controlled release materials permits the production of more uniform, spherical minicapsules or minispheres, that once exposed to various aqueous environments dissolve, resulting in perforated outer or multiple layers that may result in enhanced or further controlled degradation of the remaining melt extrudate material. Either or both of the gelling agent and the melt extrudate may contain one or more active ingredient or additional functional excipient.

The resulting extruded spherical minicapsules or minispheres may be air cooled or dropped into a cooling liquid bath, harvested and, if required, be processed to remove residual cooling liquid from the surface and then, if required, further cured at an elevated temperature.

The resulting spherical minicapsules or minispheres may be coated with additional drug layers, controlled release polymers, muco- or bio-adhesive polymers or other such coatings to enhance overall functionality or pharmacotherapeutic potential.

As an alternative to, or in addition to, the extruded spherical minicapsules or minispheres produced using a vibrational force, the extruded single- or concentric multiple-layer cylindrical extrudate may be shaped using a blade or other cutting tool as the extrudate passes through the nozzle or nozzles and is cooled or cooling. The cutting tool may submerge in a liquid. The result is a cylindrical or quasi-spherical product with one or more layer, each layer containing one or more active pharmaceutical or other ingredient.

The invention provides combination products that contain two or more active pharmaceutical compounds, which may be released concomitantly in an immediate or controlled release manner or released sequentially in an immediate or controlled release manner to provide better disease management, such as initial release of a promixal loop diuretic followed by the release of a distal loop diuretic, or chronotherapeutics.

The present invention allows for the inclusion of a wide range of extrudable or heat meltable polymers, plasticisers, gelling agents, permeability enhancers, solubility enhancers, pH regulators, disintegrents, and/or stabilisers with an effective amount of active pharmaceutical agents, heated to the appropriate temperature to result in a range of spherical forms.

The pharmaceutical formulations may be administered to a subject by any one of a range of methods known in the art. In some embodiments, the formulations are designed for oral delivery by means of inclusion of multiple minicapsules or minispheres in a hard gelatin capsule or in a sachet, either of which are suited to being administered in sprinkle form for geriatrics or paediatrics. In another embodiment, the formulations are designed for vaginal or rectal administration in the form of a suppository.

The pharmaceutical formulation may comprise other components.

The methods provided in some aspects of the present invention may comprise a single step or multiple steps for preparing the pharmaceutical formulation.

Different combinations containing any one of an active pharmaceutical compound together with one or more non-therapeutic compound components, including, but not limited to, melt extrudable polymer, placticiser, solubility enhancing agent, permeability enhancers, controlled release polymer, gelling agent or other entity will result in a range of formulations, each possessing a specific array of properties. Some processing conditions or combinations may be better suited for particular types or classes of active pharmaceutical compounds while other combinations may be better suited for other types or classes of active pharmaceutical compounds. Methods for the selection of a particular active pharmaceutical compound with suitable extrudable or meltable polymers are provided as part of the present invention.

In the invention the processing components and parameters can be readily selected. For example, it is possible to select extrudable or meltable polymers with a melting temperature that is compatible with the heat sensitivity of particular active pharmaceutical compounds or other non-therapeutic components.

The invention also facilitates the combination in a single spherical minicapsule or minisphere of active pharmaceutical compounds with different temperature sensitivities with extrudable or meltable polymers with complementary melting points and to process each within the same process but at different appropriate temperatures.

The extruder used to practice the invention may be any suitable commercially available model equipped to handle dry feed and having a solid conveying zone, one or multiple heating zones, and a vibrational nozzle comprising one or more inlet and one or more outlet. The extruder screw may be single or twin and may possess multiple separate temperature controllable heating zones. The nozzle shape and vibrational force, as well as the inlet fluid velocity, may be varied to modify the resultant particle shape and size. As an alternative to or in addition to the vibrational force a blade or other cutting tool may be used to enable the formation of fairly uniform spheres or cylindrical or other shaped pellet, depending on the die configuration or shape.

Depending on the product form required, the process may be varied through modifying the processing conditions. Such conditions include, by way of example, formulation composition, feed rate, operating temperature, extruder screw speed, residence time, heating zone length and extruder torque and/ or pressure as well as nozzle or die configuration, nozzle inlet speed, nozzle vibrational force or cutting tool speed. The result is a number of formulation formats.

The core formulation, whether semi-solid or liquid, may contain a swellable matrix that will serve to develop an internal osmotic pressure to enhance the release of the core contents once the outer shell or coating has been compromised by the intestinal or colonic environment.

The invention also facilitates the incorporation of micronised or nanoformulated actives or excipients to be released according to requirement. The nanoformulations may include lipid nanoparticles to enhance the absorption of hydrophilic and lipophilic entities.

The invention enables the incorporation of modified actives, either covalent or non-covalently modified to modify absorption, stability or immunogenicity or to direct passive or active drug delivery.

The invention also allows the incorporation of bioavailabilty enhancers, including, but not limited to, permeability enhancers and proteoglycan pump (PgP) inhibitors and inhibitors of cytochrome P450 enzymes.

The invention further allows the inclusion of proteolytic or other degradative enzymes, either in the gastro-intestinal lumen or systemically.

The invention additionally allows the inclusion of enzyme inhibitors, including, but not limited to lipase inhibitors.

In the current invention it is possible to include pH modulators (such modulators may enhance solubility), protect pH-sensitive entities, and/or modify release from minicapsules or minispheres.

It is also possible to include absorption regulators to, for example, prevent absorption of certain nutrients or metabolised subunits thereof from the intestine, including, but not limited to, lipid components, carbohydrate components, protein components. Such may include bile acid sequestrants.

It is further possible to include immunomodulating agents, including but not limited to vaccine adjuvants, allergens, anti-allergenic entities, inducers of oral tolerance and so forth.

The invention also enables the incorporation of excipients to enhance lymphatic or hepatic absorption, including, but not limited to, lipid excipients, cyclodextrins, and modified cyclodextrins.

Additionally, the invention permits the development of tamper-proof formulations of, for example, certain addictive entities through enabling combinations of the active pharmaceutical entity with an antidote, an irritant, an antibody or other such entities which when delivered orally are ineffective but, when tampered with, neutralise the active pharmaceutical effectiveness.

Furthermore, the invention permits the development of antibiotic formulations with increased residence time in the small intestine or localised release at the colonic epithelial cells to reduce colonic bacterial flora damage.

The pharmaceutical formulation, in particular for the multiple layer formats, may be a wax, emulsion, paste, cream or ointment containing the appropriate solvents (such as water, aqueous, nonaqueous, polar, nonpolar, hydropic, hydrophilic and/or combinations thereof) and optionally other compounds (stabilisers, perfumes, antimicrobial agents, antioxidants, pH modifiers, adhesives, taste masking agents, colourants, preservatives, anti-oxidants, surfactants and/or bioavailability modifiers). It is contemplated that bioavailability enhancers such as alcohols or other compounds that enhance the penetration of the therapeutic compound from the pharmaceutical formulation may be included.

For oral, buccal, and sublingual administration, the pharmaceutical formulation may be in the form of a gel cap, caplet, tablet, capsule, suspension or powder. For rectal administration, the pharmaceutical formulation may be in the form of a suppository, ointment, enema, tablet or cream for release of compound into the intestines, sigmoid flexure and/or rectum.

In solid unit dosage forms, the compounds can be combined with conventional carriers, for example: binders, such as acacia, corn starch or gelatin; disintegrating agents, such as, corn starch, guar gum, potato starch or alginic acid; lubricants, such as stearic acid or magnesium stearate; and inert fillers, such as lactose, sucrose or corn starch and the like.

Additionally, the active ingredients may be partially encapsulated, fully encapsulated, partially adsorbed complexed, fully adsorbed complexed or combinations thereof. Such encapsulation may be achieved using conventional procedures and can use water-insoluble or water-soluble agents.

For suspension preparations, the pharmaceutical formulation may include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. They may also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethylene glycol) 450, with petroleum hydrocarbons, such as mineral oil and petrolatum; with water, or with mixtures thereof; with or without the addition of a pharmaceutically suitable surfactant, suspending agent or emulsifying agent.

Oils can also be employed in the preparation of formulations of the soft gelatin type and suppositories. Water, saline, aqueous dextrose and related sugar solutions, and glycerols may be employed in the preparation of suspension formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl beta-aminopropionates and 2-alkylimidazoline quaternary ammonium salts; and mixtures thereof.

A number of hydrophobic meltable binders may be employed, including, but not limited to Beeswax, Carnauba wax, Cetyl palmitate, Glyceryl behenate, Glyceryl monostearate, Glyceryl palmitostearate, Glyceryl stearate, Hydrogenated castor oil, Microcrystalline wax, Paraffin wax, Stearic acid, Gelucire 44/01, Gelucire 35/10 and Stearic alcohol.

A number of hydrophilic meltable binders may be employed, including, but not limited to Gelucire 50/13, Gelucire 44/10, Poloxamer 188, Polyethylene glycol 2000, Polyethylene glycol 3000, Polyethylene glycol 6000, Polyethylene glycol 8000, Polyethylene glycol 10000, Polyethylene glycol 20000 and Stearate 6000 WL1644.

Some embodiments of the present invention require water-soluble agents. Such water-soluble gelling agents include, but are not limited to, gelatins, proteins, polysaccharides, starches, celluloses and combinations thereof. Other water-soluble coating materials may be comprised of, but are not limited to, albumin, pectin, guar gum, carboxymethyl starches, carboxymethyl celluloses, carrageenan, agar and similar, hydroxypropyl cellulose, polyvinyl alcohol, polyvinyl pyrrolidone, pullulan and combinations thereof.

It is contemplated that either one or a combination of immediate release, accelerated release, long-acting, sustained release, controlled release or slow release dosage forms may be used in the present invention. The course and duration of administration of and the dosage requirements for the formulation of the present invention will vary according to the subject being treated, the compound being administered, the formulation used, the method of administration used, the severity and type of indication being treated, the coadministration of other drugs and other factors.

The therapeutic compounds contained within the formulation may be formulated as their pharmaceutically acceptable salts. As used herein, "pharmaceutically acceptable salts" refers to derivatives of the disclosed compounds wherein the parent therapeutic compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, flunaric, toluenesulfonic, methanesulfonic, ethane disulfonic, oxalic, isethionic, and the like.

The pharmaceutically acceptable salts of the present invention can be synthesised from a parent therapeutic compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two. Generally, nonaqueous media are preferred. Lists of suitable salts are found in Remington's Pharmaceutical Sciences, 17th ed., Mack Publishing Company, Easton, Pa., 1985, p. 1418, the disclosure of which is hereby incorporated by reference. Additionally, the therapeutic compounds contained within the formulation may be formulated to include covalently modified variants, wherein permeability enhancing, stability enhancing, immuno-modifying or other entities including nitric oxide or nitric oxide donors are conjugated to the small molecule or biopharmaceutical therapeutic compound(s) being formulated.

The invention is not limited to the embodiments hereinbefore described which may be varied in detail.

As used in the description of the present invention, the term "effective amount" is defined as an amount or dose sufficient to elicit a physiological response in vitro or in vivo.

BRIEF DESCRIPTION OF THE DRAWINGS

The invention will be more clearly understood from the following description thereof, given by way of example only, in which.

DETAILED DESCRIPTION

Figure 1:
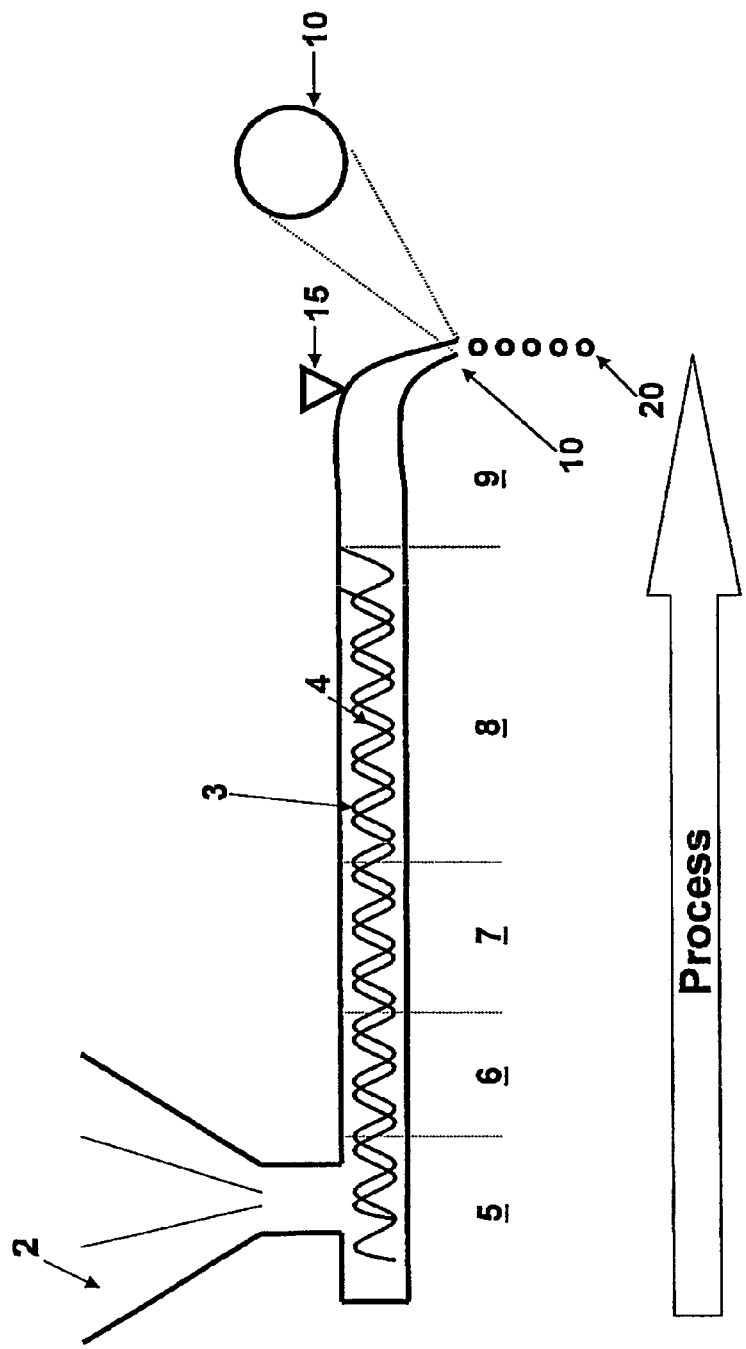
FIGS. 1 to 6 are diagrams illustrating the modified melt extrusion process of the invention.

Referring to the drawings FIG. 1 is a diagram which illustrates a modified melt extrusion process comprising a vibrating nozzle that may have single or multiple concentric passageways which permits droplet formation resulting in the formation of solid minispheres. In addition to or as an alternative to the use of a vibrational force to form the droplet, a cutting tool may also be applied.

In more detail, FIG. 1 illustrates a process to produce solid minispheres using molten extrusion through a single nozzle. The apparatus used in the process comprises an extruder 1 having a dosing hopper 2 through which various ingredients such as a drug, extrudable polymers, plasticisers and the like are introduced. The hopper 2 directs the mixture to be extruded to extruder screws 3 in a housing 4. The screw has a feeding section 5, a melting section 6, a mixing section 7, a homogenising section 8. There is also a cooling section 9 in the housing prior to discharge into a nozzle 10.

In the feeding section 5 the blend from the dosing unit 2 uniformly enters the screw chamber via one or more extruder screws 3. In the melting section 6 the blend is heated to above the glass transition temperature of the extrudable polymers. In the mixing section 7 the motion of the extruder screw further mixes the molten blend. In the homogenising section 8 the melted mixture is further homogenised and delivered to the cooling chamber 9. The nozzle 10 may be a uni- or poly- (di-, tri- or more) centric nozzle and the hot melt passes through one or other of the nozzles 10.

The nozzle 10 is subjected to a vibration energy generated by a vibrator 15 with controllable vibrational frequencies and forces.

Figure 1A:
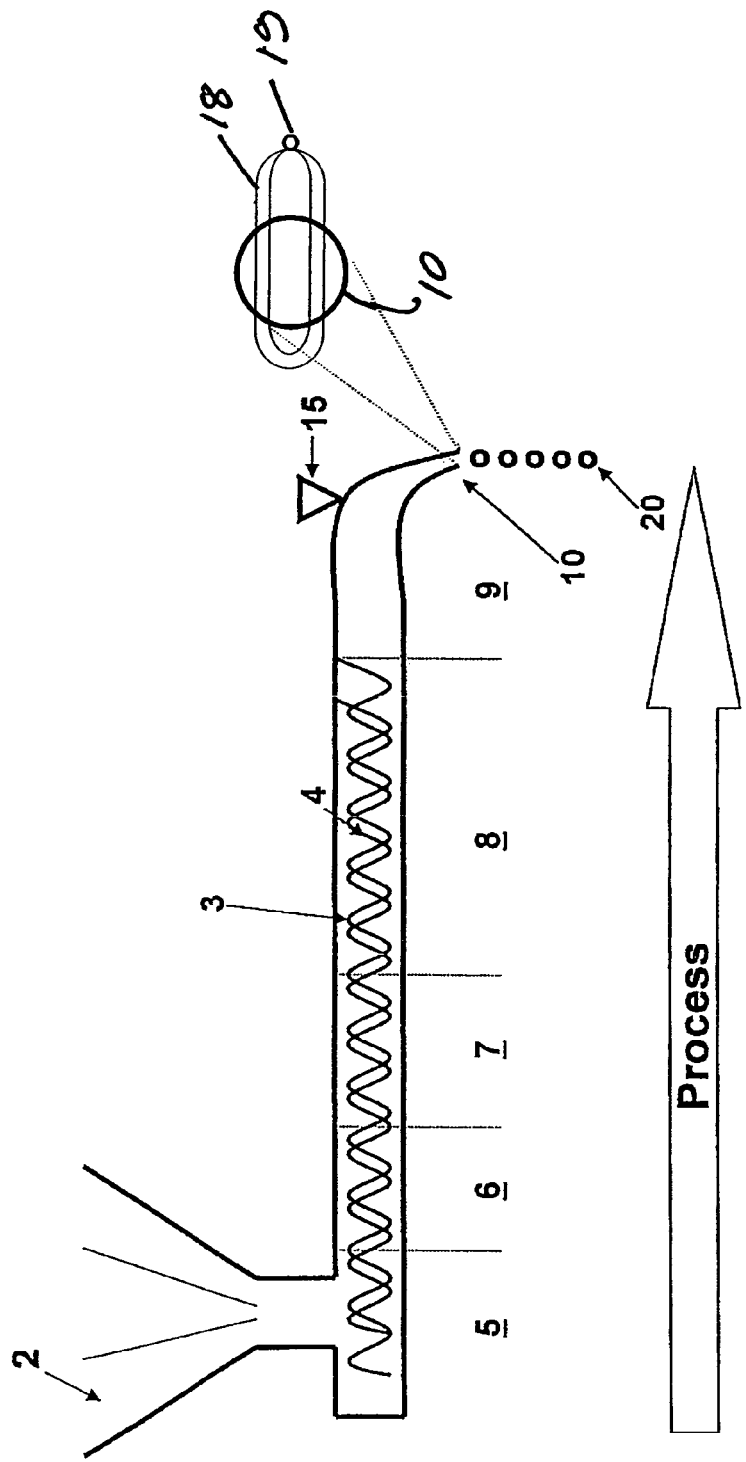

As an alternative to or in addition to a vibrator 15 the extrudate may be subjected to cutting by any suitable cutting tool such as a rotating blade 18, as illustrated in FIG. 1A, at the nozzle exit. The blade 18 rotates about a pivot 19.

The apparatus and process illustrated in FIG. 1 is used to produce solid minispheres 20.

Figure 2:
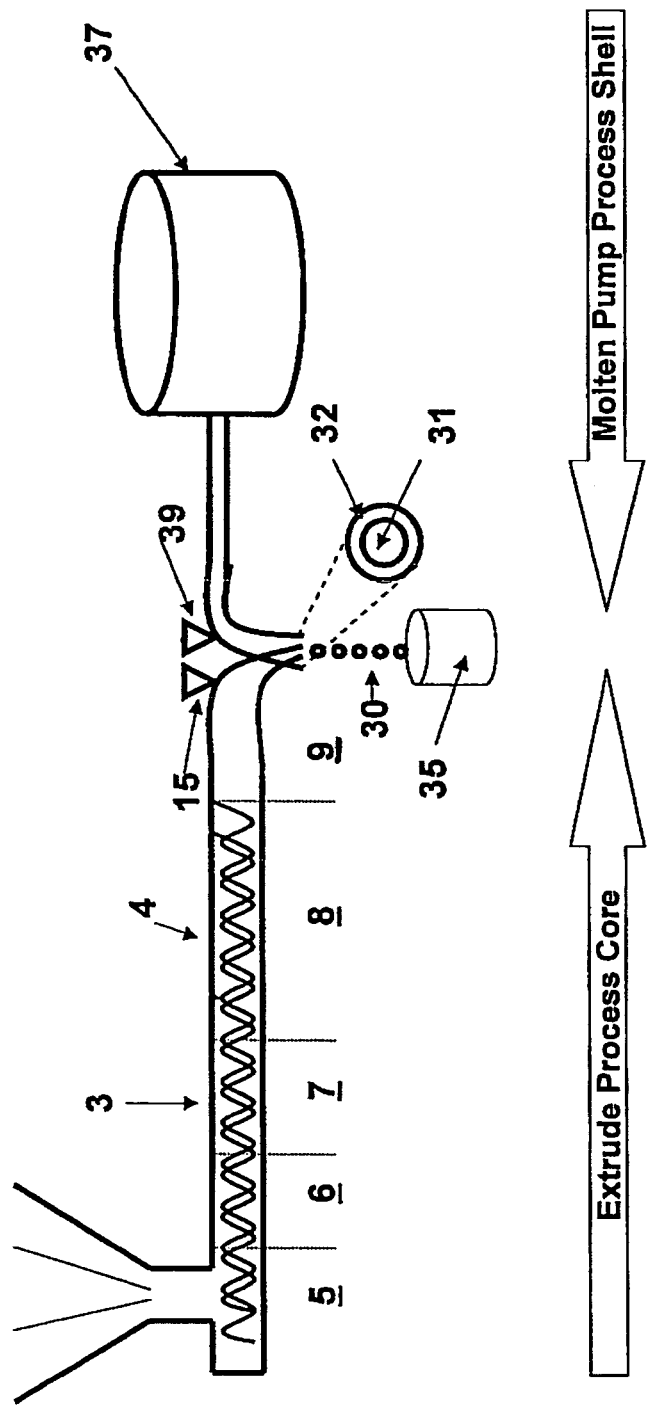

FIG. 2 is a diagram which illustrates a modified melt extrusion process comprising a vibrating nozzle that may have multiple concentric passageways through which different formulations flow. In addition to or as an alternative to the use of a vibrational force to form the droplet, a cutting tool may also be applied.

In more detail, FIG. 2 illustrates a process and an apparatus to produce a two-layered solid minisphere or liquid filled minicapsules 30. The apparatus is similar to that described with reference to FIG. 1 and like parts are assigned the same reference numerals. A shell part of the final product is processed from a molten reservoir 37 which may include a supply pump (not shown). In the reservoir 37 gelling agent is heated and pumped through a nozzle 38 to form a shell around the molten or cooled extrudate. The nozzle 38 may have a vibrator 39 to deliver controllable vibrational frequencies or forces. The nozzle is concentric and the gelatine with or without exceptions and/or with or without drug are passed through the outer 32 whilst the melt extrudable with or without drug is passed through the inner 31.

The resulting product 30 may be a multi-layered solid minisphere or liquid-filled minicapsule. The extrudate core may comprise liquid, semi-solid or solid material at ambient temperature. The outer layer may comprise a gelling agent, including melt extrudable polymers, single or complex, plasticiser, drug and/or other excipients and is mixed at elevated temperatures in a molten reservoir. All layers may contain one or more active pharmaceutical compound.

Figure 3:
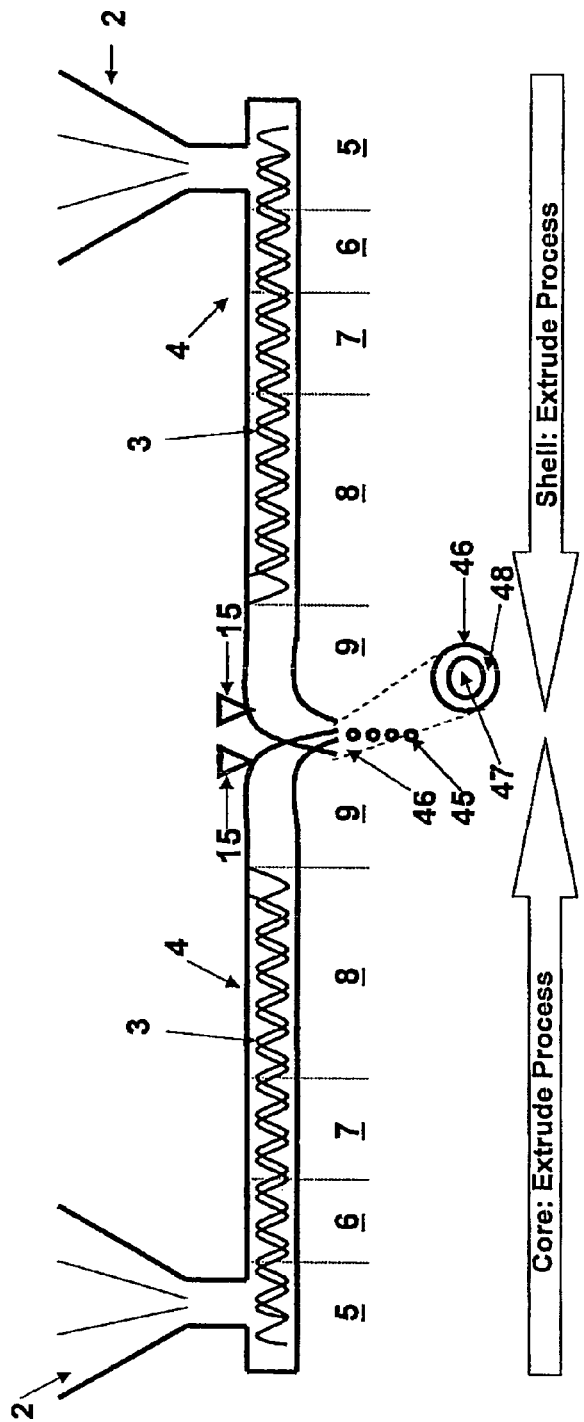

FIG. 3 is a diagram that illustrates a modified melt extrude product utilising a twin- or dual-melt extrusion process. In more detail, FIG. 3 illustrates a process and apparatus using two extruder systems 40, 41 to produce a two layer minicapsules or minisphere 45. One of the extruder systems 40 is used to process the core and the second 41 is used to process the shell. The extruder systems are each similar to those described above with reference to FIGS. 1 and 2 above and like parts are assigned the same reference numerals. There may be a common nozzle 46 with concentric inner and outer outlets 47, 48 respectively. Again, a cutting tool may be used in addition to or as an alternative to the vibrators 15. The core of the final product 45 may comprise liquid, semi-solid or solid material at ambient temperature, while the shell may comprise gelling agent, including melt extrudable polymers, single or complex, plasticiser, drug and/or other excipients.

Figure 4:
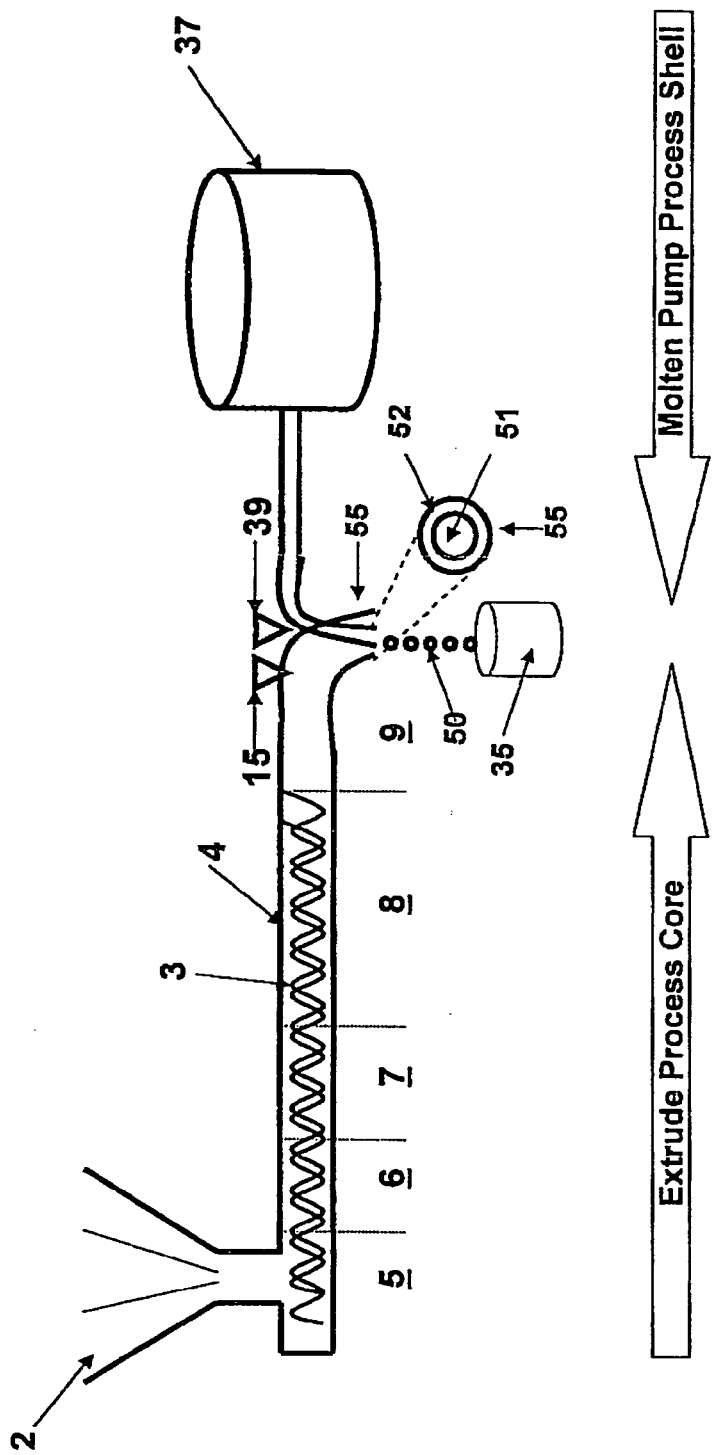

FIG. 4 is a diagram that illustrates a modified melt process, the shell of which is derived from melt extrudate from an extruder that may comprise gelling agent, including melt extrudable polymers, single or complex, plasticiser, drug and/or other excipients while the core may be comprised hydrophilic or lipophilic materials that are liquid, semi-solid or solid at ambient temperature. In addition to or rather than the use of a vibrational force to form the droplet, a cutting tool may also be applied.

In more detail, FIG. 4 illustrates a process and an apparatus to produce an inverse extrudable shell minicapsules or minisphere 50. The arrangement is similar to that of FIG. 2 and like parts are assigned the same reference numerals. The difference is that the extruder system is in this case used to extrude the shell, whilst the molten pump system is used to process the shell of the final product 50. The nozzle is concentric and the gelatine with or without excipients and/or drug are passed through the inner 51 whilst the melt extrudate with or without drug is passed through the outer 52.

Figure 5:
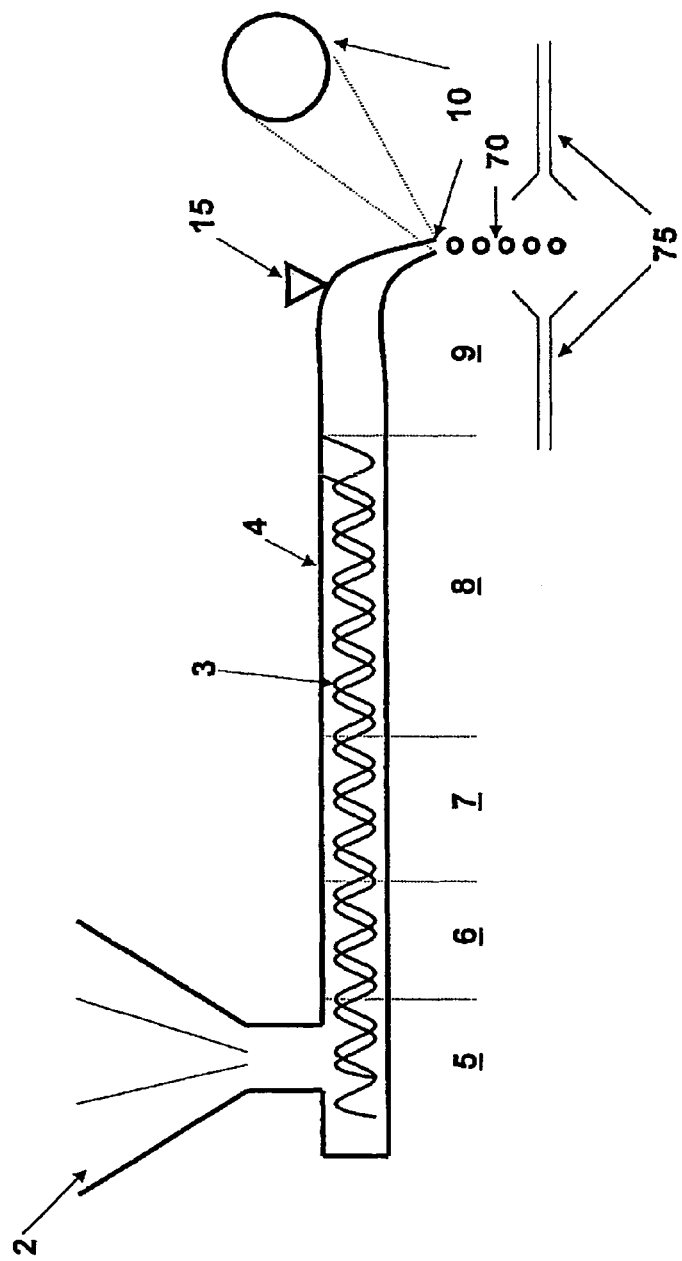

FIG. 5 is a diagram that illustrates a process and apparatus of the invention which combines melt-extrusion and spray coating. In more detail in FIG. 5, there is illustrated a process and an apparatus which combines melt-extrusion and spray coating. The system is similar to that described with reference to FIG. 1 and like parts are assigned the same reference numerals. In this case the output product 70 from the nozzle 10 is subjected to in-process or in-line spray coating 75. The core material is an extrudate produced either by conventional hot melt extrusion or the minicapsule process whereby the exiting extrudate is in solid or semi-solid spherical or non-spherical form. The spray coating occurs in a vacuum or heated chamber and the material to be coated is in solvent or otherwise readily dryable form. The resulting coated forms are harvested for further processing or otherwise. The spray coated material may comprise of controlled release polymers or other such entities, plasticisers, solvents, active entities, adhesives and so forth. The product may be further processed to add additional active or functional coats as may be desired.

Figure 6:
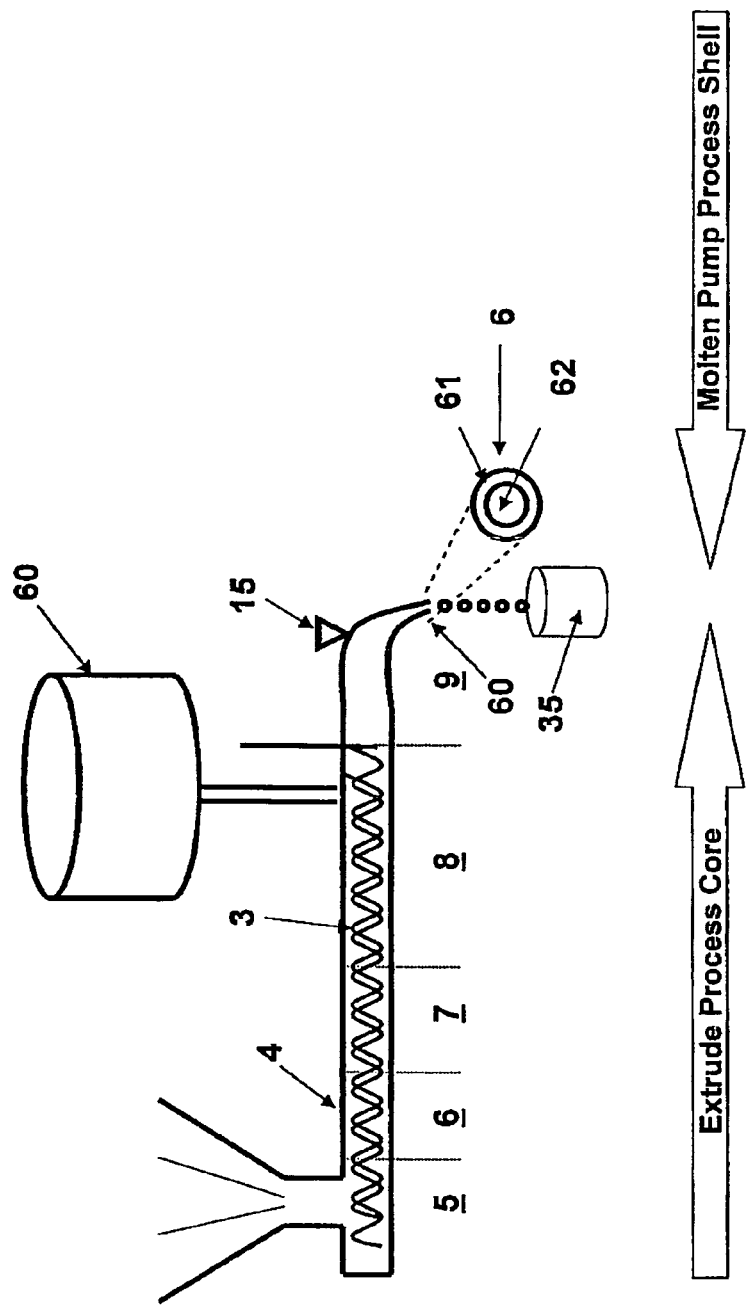

FIG. 6 is a diagram which illustrates a modified melt extrusion process comprising a vibrating nozzle that may have multiple concentric passageways through which different formulations flow. In addition to or rather than the use of a vibrational force to form the droplet, a cutting tool may also be applied. The resulting product may be a multi-layered solid minisphere or similar. The extrudate may include a gelling agent, which may be aqueous soluble, and may be introduced to the extrudate at any one or more of the feeding, melting, mixing, homogenising or cooling stages.

In FIG. 6 there is illustrated a process and an apparatus that combines melt-extrusion to include mixing with aqueous-soluble entities. The system is similar to that of FIG. 2 and like parts are assigned the same reference numerals. The difference is that in this case material from a molten reservoir 60 is heated and pumped into the molten extrudate at any suitable location such as at the mixing, homogenising or cooling section of the extruder system. The resulting product may have the gelling agent at the exterior of the form, like an encapsulating shell 61 with the non-gelling component of mix being encapsulated as a core 62 within the shell 61. Alternatively, depending on the mixing process and materials utilised the shell 61 and the core 62 may be mixed through one and other.

Figure 7:
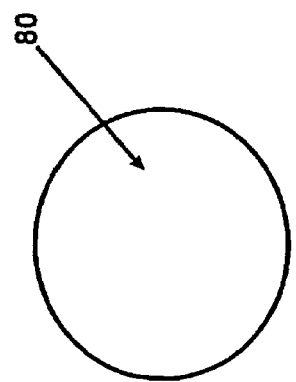

The final format, spherical or cylindrical, may comprise a gelling agent, including melt extrudable polymers, single or complex, plasticiser, drug and/or other excipients and is mixed at elevated temperatures in a molten reservoir. All layers may contain one or more active pharmaceutical compound. FIG. 7 is a diagram that illustrates a melt extrusion product using the process as per FIG. 1 or FIG. 6. The resulting single-layer product 80 may comprise of a combination including one or more of, but not limited to, melt extrusion polymers; plasticiser; active agent (pharmaceutical or nutritional); function entities, including, but not limited to disintegrants, swellable agents; hydrogels; pH modulators and so on; or gelling agents, including, but not limited to gelatine, carrageenan, chitosan (or derivatives thereof), silicon and so on. Plasticisers are selected to reduce processing temperatures and pressures as well as to stabilise the active pharmaceutical forms. The minisphere may additionally include a gelling agent to enhance form or a hydrophilic entity which will expedite dissolution in aqueous solutions. The represented products may include a swellable material to permit gastric retention of individual minispheres or enable individual minispheres to coalesce and/or adhesive molecules to enhance interaction with the mucus lining the gastric, intestinal and colonic wall or directly with the gastric, intestinal or colonic epithelial cells. The product may be further processed to add additional active or functional coats as may be desired.

Figure 8:
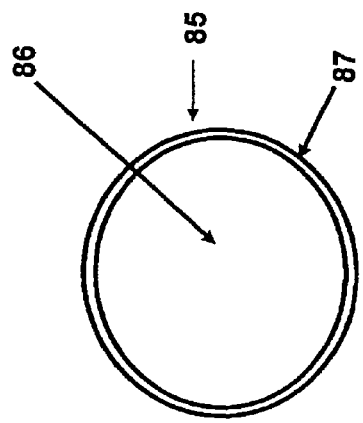

FIG. 8 is a diagram that further illustrates a product 85 produced using a process such as is illustrated in FIG. 2 wherein the core 86 comprises an extrudate that is liquid, semi-solid or solid at ambient temperature while the shell 87 comprises a gelling agent. The core 86 may comprise a combination including one or more of, but not limited to, melt extrusion polymers; plasticiser; active agent (pharmaceutical or nutritional); function entities, including, but not limited to disintegrants, swellable agents; hydrogels; pH modulators and so on while the shell is comprised of gelling agents, including, but not limited to gelatine, carrageenan, chitosan (or derivatives thereof), silicon and so on that may additionally include active agents and/or functional agents. The product may be further processed to add additional active or functional coats as may be desired.

Figure 9:
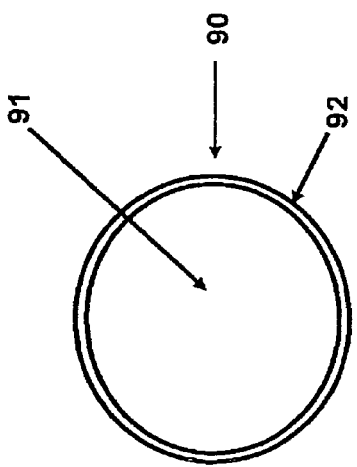
FIGS. 7 to 12 illustrate products produced using this technology.

FIG. 9 is a diagram that illustrates a product 90 produced using a process as illustrated in FIG. 3 resulting in a two-layer minicapsule or minisphere, the core 91 of which may be liquid, semi-solid or solid at ambient temperature while the shell 92 is solid and may comprise, in addition to active pharmaceutical or nutritional agents, various functional entities, including, but not limited to swellable agents, adhesive agents, disintegrants, pH modulators and so on. The product may be further processed to add additional active or functional coats as may be desired.

Figure 10:
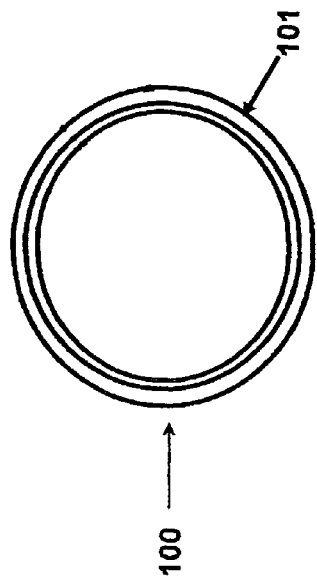

FIG. 10 is a diagram that illustrates that in addition to the product produced by any of the processes illustrated in FIGS. 1-6, the resulting one- or two-layer products 100 may have additional layers or be further coated, such coat(s) 101 include active agents, swellable material, adhesive agents, controlled release polymers, disintegrants, gelling agents and so on. Such coatings may be added in-process or using conventional coating technologies, including various fluid bed or pan coaters.

Figure 11:
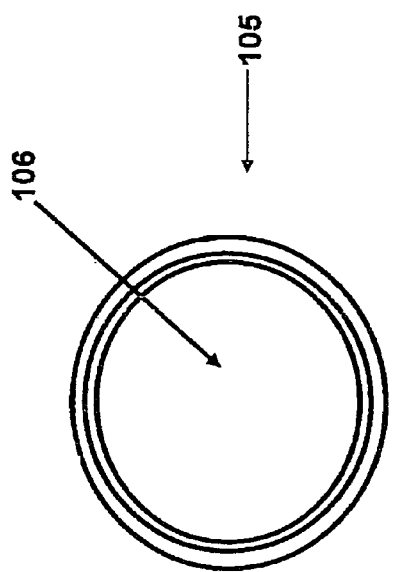

FIG. 11 is a diagram that illustrates a multi-layered minicapsule 105 containing a semi-solid or liquid core 106 that includes a hydrophilic swellable material. The swellable material may be blended with the core formulation, in the shell or in a buffer layer.

Figure 12:
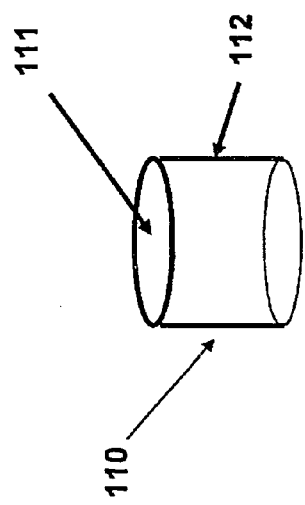

FIG. 12 is a diagramme that illustrates that in addition to the product produced by any of the processes illustrated in FIGS. 1-6, whereby the resulting one- or multi-layered products are formed through the application of a vibrational force applied to the nozzle(s) while the extrudate is in a molten state, the use of a cutting tool alone or in combination with a vibrational force to the extrudate as it exits the die(s) results in a one- or multi-layered cylindrical product 110. The core may be liquid or semi-solid with or without a gelling agent and/or a swellable material. The shell may comprise controlled release ingredients with or without gelling agent. Furthermore, the shell coating may be incomplete, permitting concurrent release or dissolution of the core and the shell.

In addition to the use of circular nozzle outlets or dies, the outlet or die may be of other shapes, including but not limited to square, rectangular, elliptical or other such forms. The resulting extrudated product will have a fairly uniform, non-spherical form.

The invention combines the benefits of both the seamless minicapsule and melt-extrusion processes. The melt-extrusion process will result in the development of a range of formulations that will address solubility and dissolution as well as other issues while the melt-extrusion process will permit more uniform particles, enhanced controlled release coatings, muco- or bio-adhesive, swellable polymers as well as other advantages. The products of the invention will be suited to further processing into hard gelatin capsules, pills, pellets, suppositories, sachets or other administration formats.

In the invention, depending on the viscosity, surface tension, temperature or other variable, the molten extrudate may be passed through a vibrating nozzle to form a spherical or other desired particle shape. The particle diameter will be dependent on the viscosity, flow rate, surface tension as well as the nozzle diameter and vibrational frequency to which the nozzle is set and/or rotational speed or force of the cutting tool at the nozzle or die tip. The cutting tool may be a rotary cutter, sheer cutter, knife, all of which may be fixed or freely rotating and may be comprised of any combination of the above. The resulting particles are then cooled in the air or dropped into or formed in a cooling liquid, harvested and, if required, cured overnight at an elevated temperature.

The die or nozzle may be a concentric nozzle comprising two or more nozzles. A film forming agent and/or polymer, including, but not limited to, gelatin and/or ethylcellulose may flow through an outer nozzle. The inner nozzle may contain a formulation that is liquid at room temperature and which remains in liquid or semi-solid at room temperature. In this embodiment, the next nozzle may contain a controlled release polymer/plasticiser mix containing one or more active pharmaceutical compounds. Further nozzles containing gelling and/or controlled release polymers with or without one or more active pharmaceutical compounds may be provided.

Many control or condition variables may be altered during the extrusion and particle forming processes to form a suitable formulation. Such variables include, but are not limited to, formulation composition, feed rate, operating temperature, extruder screw revolutions per minute, residence time, die configuration, heating zone length and extruder torque and/or pressure, nozzle configuration and vibrational frequency, cutting tool rotational frequency or force and so forth. Such conditions may be readily optimised using techniques known to those skilled in the art.

The invention provides an apparatus that is based on a melt process and a pressurised or gravitational flow vibrating nozzle wherein an active pharmaceutical agent or agents are mixed with suitable excipients that enhance solubility, permeability, stability or controlled release, the mix is then rapidly heated to melt the excipients and/or the active pharmaceutical agent or agents and either pushed or gravitationally flows through a vibrating nozzle that comprises a single nozzle or multiple concentric nozzles minicapsules. The resulting minicapsules or minispheres may comprise one, two, three or more layers, one or more of which may be liquid, semi-solid or solid. In all cases the resulting minicapsules or minispheres are of a regular spherical shape. Furthermore, the invention facilitates coating of the resulting minicapsules or minispheres to further control active pharmaceutical release, stability enhancement and/or adhesion to the intestinal or colonic mucosal or epithelial cells. Additionally, the invention permits targeted release of orally delivered formulations to specific regions of the gastrointestinal tract to maximise absorption, confer protection on the payload, to optimise treatment of diseased intestinal tissue or enhance oral bioavailability. The result is modified release compositions that in operation deliver one or more active ingredients in a unique, bimodal or multimodal manner. The present invention further provides solid oral dosage forms, sachets or suppositories containing such multiple minicapsule or minisphere controlled release compositions as well as methods for delivering one or more active ingredients to a patient in a bimodal or multimodal manner. Additionally, the invention enables one or more pharmaceutical active to be administered sequentially or concomitantly to improve disease treatment and management and to benefit from the body's natural circadian rhythms.

Compounds referred to as "hot-melt extrudable" herein are those that may be hot-melt extruded. Under standard ambient temperature and pressure conditions, a hot-melt extrudable polymer, is one that is sufficiently rigid but is capable of deformation or forming a semi-liquid state under elevated heat or pressure. Although the process and formulations described in this invention need not involve plasticisers they may be included within the scope of the invention.

The term hot-melt extrusion is a broad, all encompassing term but may cover other equivalents processes such as injection molding, hot dipping, melt casting and compression molding. Through processing by any of the above methods, the resulting formulations may be shaped as needed according to the desired mode of administration, e.g. tablets, pills, lozenges, suppositories and the like. For the purposes of this invention disclosure, the term hot melt extrusion is interchangeable with the term melt extrusion and applies not only to extrusion of molten material from traditional hot melt extrusion equipment but also to the extrusion of molten material from non-traditional hot melt extrusion equipment, including the seamless minicapsule process, modifications to either traditional hot melt extrusion equipment, modifications to the minicapsule equipment, hybrids or other possible formats whereby a molten material may be extruded by the application of force, including gravitational force.

The hot-melt extrusion process employed in some embodiments of the invention is conducted at an elevated temperature within an operating temperature range that will minimise the degradation or decomposition of the therapeutic compound during processing. The operating temperature range is generally in the range of from about 35 degree Celsius to about 160 degree Celsius, depending on the melting temperature of the polymer and/or plasticiser, as determined by the heating zone controls.

The hot-melt extrusion may be conducted employing a slurry, solid, suspension, liquid, powdered or other such feed comprising the extrudable polymer and a therapeutic compound. Dry or wet feed may be employed in the process of the present invention.

The hot-melt extrusion process is generally described as follows. An effective amount of a powdered therapeutic compound is mixed with an extrudable polymer, and in some embodiments, a plactiser is added to the mixture. The pharmaceutical compound may be added to the mix in a range of ratios, depending on the desired release profile, the pharmacological activity and toxicity of the therapeutic compound and other such considerations. The mixture is then placed in the extruder hopper and passed through the heated area of the extruder at a temperature which will melt or soften the extrudable polymer and/or plasticiser, if present, to form a matrix throughout which the therapeutic compound is dispersed. The molten or softened mixture then exits via a die, or other such element, at which time, the mixture, otherwise called the extrudate, begins to harden. Traditionally, as the extrudate is still warm or hot upon exiting the die, it has generally been chopped into distinct particles and then ground, molded, spheronised, into beads and/or tableted or otherwise processed to the desired physical form.

Although various hot-melt extrusion pharmaceutical formulations and methods for making them are known, development of simple formulations for drug delivery and methods for producing them remains a problem in the pharmaceutical industry. There continues to exist a need in the art to develop controlled-release pharmaceutical formulations, as well as improved, more efficient methods for their preparation. The invention provides a process that will increase the uniformity of the final formulation and modify the structure and functionality of the resulting spherical melt extrusion minicapsule. This removes the requirement for further processing to produce 'spheronised' melt extruded particles. Additionally, the present invention has the capacity to produce minicapsules, the core of which may be liquid, semi-solid or solid while the shell may be comprised of extrudable polymers complexes. As such, in one step, controlled release minicapsules are produced that do not require gelatine or the need to coat gelatine-shelled minicapsules with further controlled release polymers. Furthermore, removing the requirement for a gelling agent or shell comprised of such, the minicapsule payload capacity is maximised. Another benefit of the present invention is the possibility to introduce excipients to further modulate the release kinetics of both hydrophilic and hydrophobic active pharmaceutical agents from the resulting product forms. Depending on the materials incorporated, the resulting product may serve to maintain the stability of various drug formats, including various amorphous or crystalline structures. Thus, the invention introduces efficiencies into both the melt-extrusion and the minicapsule processes while introducing additional functionalities into the resulting products as well as to increase the load of active substance on a weight basis.

Hot-Melt Process Excipients and Examples

In HME formulation development, polymer choice is a critical factor to obtain the desired drug-release profile during formulation development for HME. Good polymer choice facilitates processing in the extruder. Many commercially available, pharmaceutical-grade polymers can be used in HME formulations, including derivatised cellulose, poly (methacrylate) derivative, poly(ethylene-co-vinyl acetate), poly(ethylene), poly(vinyl acetate-co-methacrylic acid), epoxy resins and caprolactones, poly(ethylene oxide), poly (ethylene glycol) and others including various waxes, fats, lipid-based excipients, including the Gelucire®, Witepsol®, Labrafil® and other ranges.

Formulation, processing conditions and processing attributes of the raw materials should be considered when choosing a polymer or polymers. For example, processing conditions typically are chosen on the basis of the rheological and thermal properties of the materials to be extruded. The conditions chosen must generate an acceptable melt viscosity for processing, but they cannot result in the degradation of any raw materials. Torque, melt pressure, and drive-motor amperage are indirect measures of melt viscosity. Torque is the measure of mechanical work needed to move material through an extruder. Melt pressure is the force generated within the extruder as materials are compacted, melted, and forced through a restriction at the end of the extrusion system such as a die. If the viscosity, torque or melt pressure is too high degradation of the drug, excipient, or additives may occur.

The HME required processing conditions are defined by equipment design, polymer selection, and the use of various additives in the formulation.

The melt viscosity of the polymer is affected by processing conditions insofar as higher processing temperatures result in lower melt viscosity. At constant temperature, as the viscosity and molecular weight of the material to extrude increases, the torque in the extruder also increases. To ensure that the torque, barrel pressure, and drive-motor amperage are within acceptable limits, plasticisers may be incorporated into the formulation.

Plasticisers work to reduce the glass transition temperature of a formulation and thus facilitate the extrusion of the material and increase the flexibility of the extrudate. Suitable plactiser selection ensures than the material can be processed in the extruder at a lower or the same temperature with lower mechanical energy thereby reducing the likelihood of degradation problems that are associated with temperature-sensitive drugs or polymers. In some formulations, a drug can act as a plasticiser during processing, examples include Ibuprofen and Itraconazole. In addition to enhancing processing conditions, plasticisers can alter the drug release rate, so a balance to ensure that there is enough plasticiser to facilitate extrusion, while maintaining the desired drug-release profile, must be struck. Also, plasticisers may act to stabilise various drug structures, including amorphous or crystalline structures.

To date, a range of HME equipment modifications have been made to generate optimum final dosage forms. Some design modifications include the screw configuration, type of extruder (single versus twin screw), temperature-zone set points along the extruder, the method of loading material into the extruder hopper (starve versus flood fed), and rate of extrusion.

Aside from equipment selection, formulation, and processing conditions, polymer selection plays an important role in the success of a HME formulation. Amongst others, three polymers that are widely used in HME include polyethylene oxide, ethylcellulose, and hypromellose, including hydroxypropylmethylcellulose (HM or HMPC). Where a quick release followed by a sustained release may be desired either for the same active pharmaceutical ingredient where a quick onset followed by sustained activity is desired or different active pharmaceutical ingredients where sequential absorption is desired the release profile may be modulated through use of different melt extrusion polymers either in concentric spherical layers or parallel sheet-like forms. Examples include the Metolose range from Shin-Etsu consisting of methylcellulose and hydroxypropyl methylcellulose, each available in several grades of different viscosity. Metolose SR is exclusively designed for a hydrophilic matrix agent having tighter specifications, which is especially suitable for this matrix system. The hydrophilic matrix system is the simplest sustained release technology for oral dosage forms, consisting essentially of a drug and a water-soluble high viscous polymer. Varying the composition can permit both immediate and sustained release of a single or multiple active pharmaceutical ingredient(s).

Poly(ethylene) oxide (PEO) is a white, free-flowing hydrophilic powder. It is a highly crystalline polymer available in 100,000-7,000,000-Da molecular weights. It is currently used in the pharmaceutical industry in applications such as controlled-release, solid-dose matrix systems, transdermal drug delivery systems, and mucosal bioadhesives. PEO is an ideal candidate for HME because of its broad processing window. The crystalline melting point of PEO is ~70° C., depending upon molecular weight. Without plasticisers, PEO can be extruded at processing temperatures modestly higher than its melting point, subject to equipment limitations. The potential degradation of PEO during extrusion was reduced with the addition of vitamin E succinate, vitamin E, or vitamin E TPGS, which limit molecular weight loss of the PEO (K. Coppens et al. "Thermal and Rheological Evaluation of Pharmaceutical Excipients for Hot Melt Extrusion," paper presented at the 2004 AAPS Annual Meeting and Exposition, Baltimore, Md.).

Repka et al. ("Production and Characterization of Hot-Melt Extruded Films Containing Clotrimazole," *Drug Dev. Ind. Pharm.* 29 (7), 757-765 (2003)) suggested that HME-produced dosage forms can improve patient compliance. They argued that HME can be used to produce higher-efficiency dosage forms, thereby decreasing dose frequency (21). This study involved PEO MW 100,000 in combination with HPC and the active ingredient polycarbophil (Noveon AA-1) to produce films with thicknesses of 0.34-0.36 mm. A single-screw extruder (Killion, KLB-100) with a film die was used. PEG 3350 was added to the formulation as a plasticiser with butylated hydroxytoluene and propyl gallate as antioxidants and clotrimazole (10% w/w) as an antifungal. The exact composition of the film was not disclosed. These films were reported to have excellent content uniformity. Wide-angle X-ray diffraction studies showed that clotrimazole was molecularly dispersed within the HME films. The clotrimazole showed zero-order release over 6 hours, and prolonged release over 10 hours.

Schachter ("Solid Solution of a Poorly Soluble Model Drug in a Phase-Separated Polymer Matrix: Melt-Prepared Dispersions based on POLYOX WSR," presented at the 30th Annual Meeting of the Controlled Release Society, Glasgow, Scotland, July 2003) investigated PEO MW 100,000 for preparing solid-melt dispersions with ketoprofen. Neat ketoprofen has a strong melting transition. Differential scanning calorimetry (DSC) and X-ray diffraction (XRD) analysis on the blended material suggested that ketoprofen dissolved in the amorphous phase of PEO. The dispersion was stable, as indicated by XRD analysis of the samples stored at accelerated conditions (40° C. and 75% RH) for one month. The authors also tested the ability of PEO to form solid dispersions with other drug structures. DSC results indicated that ibuprofen, tolbutamide, sulfathiazole, and hydroflumethazide can potentially form solid dispersions in PEO. Solid-state nuclear magnetic resonance (SSNMR) results showed the PEO-ketoprofen interactions were strong enough to disrupt the crystalline lattice of ketoprofen, even at temperatures below the melting point of either component. The authors reported an increase in mobility of ketoprofen in the blend relative to the neat crystalline structure. These results confirmed the ability of PEO to form solid dispersions with ketoprofen at low temperatures.

Ethylcellulose (EC) is a hydrophobic ethyl ether of cellulose. EC is currently used in pharmaceutical applications for microencapsulation of actives, controlled-release matrix systems, taste masking, solvent and extrusion granulation, tablet binding, and as a controlled-release coating for tablets and beads. EC is available in various molecular weights, and has a $T_g$ of 129-133° C. and a crystalline melting point ~180° C. EC is a good candidate for extrusion because it exhibits thermoplastic behavior at temperatures above its glass transition temperature and below the temperature at which it exhibits degradation (~250° C.) (K. Coppens et al. "Thermal and Rheological Evaluation of Pharmaceutical Excipients for Hot Melt Extrusion," paper presented at the 2004 AAPS Annual Meeting and Exposition, Baltimore, Md.).

DeBrabander et al. studied modifying the release rate of ibuprofen from EC by adding hydrophilic excipients (HM) ("Development and Evaluation of Sustained Release Mini-Matrices Prepared via Hot Melt Extrusion," *J. Controled Release* 89 (2), 235-247 (2003)). They used a co-rotating twin-screw extruder with a 3-mm die to produce mini-matricies. The extrudate was manually cut into dosage forms 2 mm in length. Varying the ratio of HM to EC in the formulation varied the drug-release rate, with release rates increasing as the ratio of HM increased. The authors also studied the thermal stability of ibuprofen after it was extruded with polymers. The authors found that 98.9% of the ibuprofen amount remained after extrusion, as determined by high-performance liquid chromatography.

Hypromellose (HM), an hydrophilic cellulose ether, is available in a range of viscosities and substitutions. It is used in pharmaceutical applications such as controlled-release matrices, tablet coatings, and granulation binders. HM has a $T_g$ of 160-210° C. and shows significant degradation at temperatures in excess of 250° C., depending upon the substitution. It has proven challenging to extrude because of its high $T_g$ and low degradation temperature, which gives HM a narrow processing window. One way to broaden the processing window is to incorporate high amounts of plasticiser in the formulation as described by Alderman and Wolford ("Sustained Release Dosage Form based on Highly Plasticised Cellulose Ether Gels," U.S. Pat. No. 4,678,516, Jul. 7, 1987). The authors suggested using at least 30% by weight of a plasticiser in an extruded matrix formulation.

Verreck, Six, and colleagues studied solid dispersions of itraconazole (a Class II drug) and HM ("Characterization of Solid Dispersions of Itraconazole and Hydroxypropylmethylcellulose Prepared by Melt Extrusion—Part I," *Int. J. Pharm.* 251 (1-2) 165-174 (2003)). Initial results indicated an amorphous solid dispersion of itraconazole in HM was formed. HME was used to study blends of 40% itraconazole and 60% HM. Samples produced using a co-rotating twin-screw extruder followed by milling milled released 90% of the itraconazole in 120 min. Samples made with a physical mixture of the drug and the polymer released only 2% of the intraconazole in the same time period. In a study to improve the dissolution rate of itraconazole, the extrudate was milled and a formulation comprising 25% itraconazole, 75% HM, 80% of the drug was dissolved within 30 min. These results are in contrast with dissolution of crystalline and glassy itraconazole, which had 0% and 5% drug release after 30 min, respectively.

Rambali et al. optimised a HME formulation containing itraconazole, HM, and hydroxypropyl-β-cyclodextrin (HP-β-CD) ("Itraconazole Formulation Studies of the Melt-Extrusion Process with Mixture Design," *Drug Dev. Ind. Pharm.* 29 (6), 641-652 (2003)). The authors reported that itraconazole acted as a plasticiser for the melt because formulations with higher drug loading had a lower torque. For example, a formulation with 60% HM, 20% (HP-β-CD), and 20% itraconazole had a torque of 45%. When the percentage of itraconazole was increased to 43%, with 37% HM and 20% (HP-β-CD), the torque was reduced to 34%. A twin screw co-rotating extruder with a 3.0-mm rod-shaped die was used to generate these observations.

EC and HM can be combined in unique dosage forms to deliver active pharmaceuticals. One of these dosage forms used an EC outer pipe and a separately prepared HM core ("Hot-Melt Extruded Ethylcellulose Cylinders Containing a HPMC-Gelucire Core for Sustained Drug Delivery," *J. Controled Release* 94 (2-3), 273280 (2004)). The EC pipe was produced using HME with a laboratory-scale twin-screw co-rotating extruder with an annular die with a metal insert to produce the pipes. The core was manually prepared by heating the components until molten, followed by homogenization. The core material was manually filled into the pipe. The authors suggest that the entire process could be automated in a full-scale HME production operation. The goal of this study was to eliminate the burst effect that is sometimes seen in HM matrix tablets. It was reported that with a 5% drug loading of theophylline monohydrate (medium soluble, aqueous solubility 8.33 g/L), propranolol HCl (freely water soluble, aqueous solubility 50 g/L), or hydrochlorothiazide (poorly soluble, 0.1 N HCl solubility 0.25 g/L) drug solubility did not affect release rate. Instead, the dissolution profiles indicated erosion-controlled, zero-order drug release for all three drugs. The authors also examined the effect of viscosity grade and substitution type of HM used in the inner core. The authors found that for the same HM viscosity, there was no difference in release rates. Nonetheless, replacing HM with methylcellulose (MC) resulted in faster release rates.

Another study by Mehuys et al. reported an increase in the bioavailability of propranolol HCl when an EC pipe with HM-Gelucire core was used instead of the core alone ("In Vitro and in Vivo Evaluation of a Matrix-in-Cylinder System for Sustained Drug Delivery," *J. Controled Release* 96 (2), 261-271 (2004)). The EC pipes were produced with a laboratory-scale co-rotating twin-screw extruder with an annular die with metal insert to produce the pipes. The pipes had a 5-mm internal diameter, a 1-mm wall thickness, and were cut into 12-mm lengths. The core materials were heated until molten and then homogenised. The pipe cores were manually filled with the separately prepared HM-Gelucire core material. The authors reported that hydrodynamics, mechanical stress, and the dissolution medium had little effect on drug-release rates. Results indicated that the HME-produced matrix in cylinder propranolol HCl had better bioavailability in dogs compared with the Inderal (Wyeth) sustained-release formulation. The authors reported the relative bioavailability of the matrix in cylinder system was ~400% better than Inderal, measured by the mean AUCO-24.

U.S. Pat. No. 6,391,338 (Biovail Inc.) discloses a hot melt formulation comprising either the pharmaceutical actives ibuprofen or nifedipine within a sustained release core composed primarily of Eudragit® E100. The compositions have an amount of ibuprofen or nifedipine available for sustained release following oral administration from the gastric environment to the colon.

Controlled Release Polymers—Membrane-Controlled Dosage Forms

The modified-release formulations of the present invention can also be provided as membrane-controlled formulations. Membrane-controlled formulations of the present disclosure can be made by preparing a rapid release core, which can be liquid, semi-solid or solid, encapsulated by a gelatin shell, and coating the shell a functional coating. In the presence or absence of the membrane-controlled coating, the core, whether liquid, semi-solid or solid, can be formulated such that it itself controlled the release rate of the pharmaceutical compound from the minicapsules Details of membrane-controlled dosage forms are provided below.

In certain embodiments of the current invention, the pharmaceutical compound is provided in a multiple minicapsule membrane-controlled formulation. The active pharmaceutical can be formulated as a liquid, semi-solid or solid entity to enhance solubility, permeability or dissolution rate and utilised as the core of a two- or three-layer minicapsule that additionally comprises a shell with or without an additional buffer layer between to separate miscible core and shell constituents. The minicapsule diameter may range from 0.5 to about 5.0 mm. Additional pharmaceutral compound of the same active or one or more other actives can be sprayed from solution or suspension using a fluidised-bed coater or pan coating system.

To control the location of formulation release from the minicapsules, various delayed-release and/or extended-release polymeric materials, applied as a membrane coating to the minicapsules. The polymeric materials include both water-soluble and water-insoluble polymers. Possible water-soluble polymers include, but are not limited to, polyvinyl alcohol, polyvinylpyrrolidone, methylcellulose, hydroxypropylcellulose, hydroxypropylmethyl cellulose or polyethylene glycol, and/or mixtures thereof.

Possible water-insoluble polymers include, but are not limited to, ethylcellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(ethylene oxide), poly(ethylene terephthalate), poly(vinyl isobutyl ether), poly(vinyl acetate), poly(vinyl chloride), or polyurethane, and/or mixtures thereof.

EUDRAGIT®™ polymers (available from Evonik) are polymeric lacquer substances based on acrylates and/or methacrylates. A suitable polymer that is freely permeable to the active ingredient and water is EUDRAGIT® RL. A suitable polymer that is slightly permeable to the active ingredient and water is EUDRAGIT® RS. Other suitable polymers that are slightly permeable to the active ingredient and water, and exhibit a pH-dependent permeability include, but are not limited to, EUDRAGIT® L, EUDRAGIT® S, and EUDRAGIT® E.

EUDRAGIT® RL and RS are acrylic resins comprising copolymers of acrylic and methacrylic acid esters with a low content of quaternary ammonium groups. The ammonium groups are present as salts and give rise to the permeability of the lacquer films. EUDRAGIT® RL and RS are freely permeable (RL) and slightly permeable (RS), respectively, independent of pH. The polymers swell in water and digestive juices, in a pH-independent manner. In the swollen state, they are permeable to water and to dissolved active compounds.

EUDRAGIT® L is an anionic polymer synthesised from methacrylic acid and methacrylic acid methyl ester. It is insoluble in acids and pure water. It becomes soluble in neutral to weakly alkaline conditions. The permeability of EUDRAGIT® L is pH dependent. Above pH 5.0, the polymer becomes increasingly permeable.

In various embodiments comprising a membrane-controlled dosage form, the polymeric material comprises methacrylic acid co-polymers, ammonio methacrylate co-polymers, or mixtures thereof. Methacrylic acid co-polymers such as EUDRAGIT® S and EUDRAGIT® L (Evonik) are suitable for use in the controlled release formulations of the present invention. These polymers are gastroresistant and enterosoluble polymers. Their polymer films are insoluble in pure water and diluted acids. They dissolve at higher pHs, depending on their content of carboxylic acid. EUDRAGIT® S and EUDRAGIT® L can be used as single components in the polymer coating or in combination, in any ratio. By using a combination of the polymers, the polymeric material can exhibit solubility at a pH between the pHs at which EUDRAGIT® L and EUDRAGIT® S are separately soluble.

The membrane coating can comprise a polymeric material comprising a major proportion (i.e., greater than 50% of the total polymeric content) of at least one pharmaceutically acceptable water-soluble polymers, and optionally a minor proportion (i.e., less than 50% of the total polymeric content) of at least one pharmaceutically acceptable water insoluble polymers. Alternatively, the membrane coating can comprise a polymeric material comprising a major proportion (i.e., greater than 50% of the total polymeric content) of at least one pharmaceutically acceptable water insoluble polymers, and optionally a minor proportion (i.e., less than 50% of the total polymeric content) of at least one pharmaceutically acceptable water-soluble polymer.

The amino methacrylate co-polymers can be combined in any desired ratio, and the ratio can be modified to modify the rate of drug release. For example, a ratio of EUDRAGIT® RS:EUDRAGIT® RL of 90:10 can be used. Alternatively, the ratio of EUDRAGIT® RS:EUDRAGIT® RL can be about 100:0 to about 80:20, or about 100:0 to about 90:10, or any ratio in between. In such formulations, the less permeable polymer EUDRAGIT® RS would generally comprise the majority of the polymeric material with the more soluble RL, when it dissolves, permitting creating gaps through which solutes can enter the core and dissolved pharmaceutical actives escape in a controlled manner.

The amino methacrylate co-polymers can be combined with the methacrylic acid co-polymers within the polymeric material in order to achieve the desired delay in the release of the drug. Ratios of ammonio methacrylate co-polymer (e.g., EUDRAGIT® RS) to methacrylic acid co-polymer in the range of about 99:1 to about 20:80 can be used. The two types of polymers can also be combined into the same polymeric material, or provided as separate coats that are applied to the core.

In addition to the EUDRAGIT® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate.

Surelease®, an aqueous ethylcellulose dispersion developed by Colorcon, is a unique combination of film-forming polymer; plasticiser and stabilisers. Designed for sustained release and taste masking applications, Surelease® is an easy-to-use, totally aqueous coating system using ethylcellulose as the release rate controlling polymer. The dispersion provides the flexibility to adjust drug release rates with reproducible profiles that are relatively insensitive to pH.

The principal means of drug release is by diffusion through the Surelease®dispersion membrane and is directly controlled by film thickness. Increasing or decreasing the quantity of Surelease®applied can easily modify the rate of release.

With Surelease®dispersion, reproducible drug release profiles are consistent right through from development to scale-up and production processes. More information can be found on the Colorcon Inc website at www. Colorcon.com.

A range of additional materials may be employed to enable controlled release coating. Additionally, any combination of Eudragit®, Surelease® or other polymers or materials may be utilised.

The coating membrane can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose, and sucrose, sugar alcohols such as lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer. The coating process can be carried out by any suitable means, for example, by using a perforated pan system such as the GLATT, ACCELACOTA, and/or HICOATER processing equipment.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566.

With membrane-modified extended-release dosage forms, a semi-permeable membrane can surround the formulation containing the active substance of interest. Semi-permeable membranes include those that are permeable to a greater or lesser extent to both water and solute. This membrane can include water-insoluble and/or water-soluble polymers, and can exhibit pH-dependent and/or pH-independent solubility characteristics. Polymers of these types are described in detail below. Generally, the characteristics of the polymeric membrane, which may be determined by, e.g., the composition of the membrane, will determine the nature of release from the dosage form.

A number of modified dosage forms suitable for use are described below. A more detailed discussion of such forms can also be found in, for example The Handbook of Pharmaceutical Controlled Release Technology, D. L. Wise (ed.), Marcel Decker, Inc., New York (2000); and also in Treatise on Controlled Drug Delivery: Fundamentals, Optimization, and Applications, A. Kydonieus (ed.), Marcel Decker, Inc., New York, (1992), the relevant contents of each of which are hereby incorporated by reference for this purpose. Examples of modified-release formulations include but are not limited to, membrane-modified, matrix, osmotic, and ion-exchange systems. All of these can be in the form of single-unit or multi-unit dosage forms, as alluded to above.

Colonic Delivery Coatings and Formulations

Oral delivery of drugs to the colon is valuable in the treatment of diseases of colon (ulcerative colitis, Chron's disease, carcinomas and infections) whereby high local concentration can be achieved while minimizing side effects that occur because of release of drugs in the upper GIT or unnecessary systemic absorption. The colon is rich in lymphoid tissue, uptake of antigens into the mast cells of the colonic mucosa produces rapid local production of antibodies and this helps in efficient vaccine delivery (Sarasija, S, and Hota, A., Colon-specific drug delivery systems. *Ind J Pharm Sci,* 62: 1-8, 2000). The colon is attracting interest as a site where poorly absorbed drug molecule may have an improved bioavailability. This region of the colon is recognised as having a somewhat less hostile environment with less diversity and intensity of activity than the stomach and small intestine. Additionally, the colon has a longer retention time and appears highly responsive to agents that enhance the absorption of poorly absorbed drugs. Apart from retarding or targeting dosage forms, a reliable colonic drug delivery could also be an important starting position for the colonic absorption of perorally applied, undigested, unchanged and fully active peptide drugs. As the large intestine is relatively free of peptidases such special delivery systems will have a fair chance to get their drug sufficiently absorbed after peroral application. The simplest method for targeting of drugs to the colon is to obtain slower release rates or longer release periods by the application of thicker layers of conventional enteric coatings or extremely slow releasing matrices.

The various strategies for targeting orally administered drugs to the colon include covalent linkage of a drug with a carrier, coating with pH-sensitive polymers, formulation of timed released systems, exploitation of carriers that are degraded specifically by colonic bacteria, bioadhesive systems and osmotic controlled drug delivery systems. Various prodrugs (sulfasalazine, ipsalazine, balsalazine and olsalazine) have been developed that are aimed to deliver 5-amino salicylic acid (5-ASA) for localised chemotherapy of inflammatory bowel disease (IBD). Microbially degradable polymers especially azo crosslinked polymers have been investigated for use in targeting of drugs to colon. Certain plant polysaccharides such as amylose, inulin, pectin and guar gum remains unaffected in the presence of gastrointestinal enzymes and pave the way for the formulation of colon targeted drug delivery systems. The concept of using pH as a rigger to release a drug in the colon is based on the pH conditions that vary continuously down the gastrointestinal tract. Time dependent drug delivery systems have been developed that are based on the principle to prevent release of drug until 3-4 h after leaving the stomach. Redox sensitive polymers and bioadhesive systems have also been exploited to deliver the drugs into the colon.

The pH-dependent systems exploit the generally accepted view that pH of the human GIT increases progressively from the stomach (pH 1-2 which increases to 4 during digestion), small intestine (pH 6-7) at the site of digestion and it increases to 7-8 in the distal ileum. The coating of pH-sensitive polymers to the tablets, capsules or pellets provide delayed release and protect the active drug from gastric fluid. The polymers used for colon targeting, however, should be able to withstand the lower pH values of the stomach and of the proximal part of the small intestine and also be able to disintegrate at the neutral of slightly alkaline pH of the terminal ileum and preferably at the ileocecal junction.

The GI residence time of the dosage forms is another important parameter for pH-dependent colon targeted drug delivery systems which is influenced by many physiological and other factors; nevertheless, there are some generally accepted GI residence values for various parts of the GIT. Most commonly used pH-dependent coating polymers are methacrylic acid copolymers, commonly known as Eudragit® S (Registered trademark of Evonik AG, Darmstadt, Germany), more specifically Eudragit® L and Eudragit® S. Eudragit® L100 and S 100 are copolymers of methacrylic acid and methyl methacrylate. The ratio, of carboxyl to ester groups is approximately 1:1 in Eudragit® L100 and 1:2 in Eudragit® S 100. The polymers form salts and dissolve above pH 5.5 and disperse in water to form latex and thus avoid the use of organic solvents in the coating process. Eudragit® L30D-55 is a ready to use aqueous dispersion of Eudragit®® L100-55. The water solubility of the Eudragit® S depends on the ratio of free carboxyl groups to the esterifies groups. The critical factor that influences the performance of these polymers is the pH value at which dissolution occurs. Polymers with ionizable phthalic acid groups dissolve much faster and at a lower pH than those with acrylic or methacrylic acid groups. The presence of plasticiser (81) and the nature of the salt (82, 83) in the dissolution medium also influence the dissolution rate of Eudragit®. In addition, the permeability of the film formed may depend on the type of solvent used to dissolve Eudragit® (Dressman, J. B., Amidon, C., Reppas, C. and Shah, V. P., Dissolution testing as a prognostic tool for oral drug absorption: Immediate release dosage forms, Pharm Res, 15: 11-22, 1998.).

Polysaccharides, the polymer of monosaccharides retains their integrity because they are resistant to the digestive action of gastrointestinal enzymes. The matrices of polysaccharides are assumed to remain intact in the physiological environment of stomach and small intestine but once they reach in the colon, they are acted upon by the bacterial polysaccharides and results in the degradation of the matrices. This family of natural polymers has an appeal to the area of drug delivery as it is comprised of polymers with a large number of derivatizable groups, a wide range of molecular weights, varying chemical compositions, and for the most part, a low toxicity and biodegradability, yet a high stability. The most favorable property of these materials is that they are already approved as pharmaceutical excipients. A large number of polysaccharides such as amylose, guar gum, pectin, chitosan, inulin, cyclodextrins, chondroitin sulphate, dextrans and locust bean gum have been investigated for their use in colon targeted drug delivery systems. The most important fact in the development of polysaccharide derivatives for colon targeted drug delivery is the selection of a suitable biodegradable polysaccharide. As these polysaccharides are usually soluble in water, they must be made water insoluble by crosslinking or hydrophobic derivatisation.

Guar gum is hydrophilic in nature and swells in cold water forming viscous colloidal dispersions or sols. This gelling property retards release of the drug from the dosage form as well as it is susceptible to degradation in the colonic environment. Homogenised and diluted feces from human source were incubated with the guar gum to investigate the degradation of polysaccharide by intestinal microflora. It produced a rapid decrease in viscosity and fall in pH while no such results were observed when it was incubated with autoclaved fecal homogenates. Guar gum was crosslinked with increasing amounts of trisodium trimetaphosphate to reduce its swelling properties for use as a vehicle in oral delivery formulations. As a result of the crosslinking procedure guar gum lost its non-ionic nature and became negatively charged. This was demonstrated, by methylene blue adsorption studies and swelling studies in sodium chloride solutions with increasing concentrations in which the hydrogels' network collapsed (Gliko-Kabir, I., Yagen, B., Penhasi, A. and Rubinstein, A., Phosphated crosslinked guar for colon-specific drug delivery. I. Preparation and physicochemical characterization. J Control Rel, 63: 121-127, 2000). Crosslinked guar gum products were analysed to check the efficacy as colon-specific drug carrier and it was found that the product which was crosslinked with 0.1 equivalent of trisodium trimetaphosphate was able to prevent the release of 80% of its hydrocortisone load for at least 6 h in PBS (pH 6.4). When a mixture of galactosidase and mannanase or derivatives thereof was added to the buffer solution, an enhanced release was observed. In vivo degradation studies in the rat caecum showed that despite the chemical modification of guar gum, it retained its enzyme-degrading properties in a crosslinker concentration dependent manner. A novel tablet formulation for oral administration using guar gum as the carrier and indomethacin as a model drug has been investigated for colon targeted drug delivery using in vitro methods. Drug release studies under conditions simulating the gastrointestinal transit have shown that guar gum protects the drug from being released completely in the physiological environment of stomach and small intestine. Studies in pH 6.8 PBS containing rat caecal contents have demonstrated the susceptibility of guar gum to the colonic bacterial enzyme action with consequent drug release (Rama Prasad, Y. V., Krishnaiah, Y. S. R. and Satyanarayana, S., In vitro evaluation of guar gum as a carrier for colon-specific drug delivery. J Control Rel. 51: 281-287, 1998).

Colon-specific drug delivery may be possible by the application of dried amylose films to pharmaceutical formulations. Amylose, one of the major fractions of starch, possesses the ability to form films through gelation, when prepared under appropriate conditions. The microstructure of the film is potentially resistant to the action of pancreatic α-amylase but is digested by amylases of the colonic microflora. However, under simulated gastrointestinal conditions, coatings made solely of amylose will become porous and allow drug release. Incorporation of insoluble polymers into the amylose film, to control amylose swelling, provides a solution to this problem. A range of cellulose and acrylate based copolymers were assessed, of which a commercially available ethylcellulose (Ethocel) was found to control the swelling most effectively. The in vitro dissolution of various coated pellets under simulated gastric and small intestinal conditions, using commercially available pepsin and pancreatin was determined and demonstrated the resistance of the amylose-Ethocel coat (1:4) to such conditions over a period of 12 h (Milojevic, S., Newton, J. M., Cummings, J. H., Gibson, G. R., Botham, R. L., Ring, S. C., Stockham, M. and Allwood, M. C., Amylose as a coating for drug delivery the colon: Preparation and in vitro evaluation using 5-aminosalicylic acid pellets. J Control Rel, 38: 75-84, 1996). A further study demonstrated that coated pellets demonstrated reproducible drug release rates that were unaffected by upper gastrointestinal pH and enzymes and also long-term storage. Drug release was modified by varying parameters such as the ratio of amylose to ethylcellulose in the film and the coat thickness. Modeling of the resultant, data found that the ratio was more important than coat thickness in controlling drug release, irrespective of the solvent used for coating. Formulations comprising 1 part amylose and 1 part ethylcellulose of coat thickness, 15% TWG, successfully resisted 5-aminosalicylic acid release in the upper gastrointestinal tract yet gave a relatively rapid onset of release in simulated colonic conditions. Such organic-based systems offer a practical means of delivering drugs to the colon, particularly those that are water-sensitive and/or thermolabile (Siew et al., AAPS Pharm Sci Tech: 2000; 1 (3) article 22).

Chitosan is a high molecular weight polycationic polysaccharide derived from naturally occurring chitin by alkaline deacetylation. Chemically, it is a poly (N-glucosamine). Chitosan has favourable biological properties such as nontoxicity, biocompatibility and biodegradability. Similar to other polysaccharides it also undergoes degradation by the action of colonic microflora and hence poses its candidature for colon targeted drug delivery. Tozaki et al. (Tozaki, H., Odoriba, T., Okada, N., Fujita, T., Terabe, A., Suzuki, T., Okabe, S., Murnishi, S, and Yamamoto, A., Chitosan capsules for colon-specific drug delivery: enhanced localization of 5-aminosalicylic acid in the large intestine accelerates healing of TNBS-induced colitis in rats. J Control Rel, 82, 51-61, 2002) developed colon-specific insulin delivery with chitosan capsules. In vitro drug release experiments from chitosan capsules containing 5(6)-carboxyfluorescein (CF) were carried out by rotating basket method with slight modifications. The intestinal absorption of insulin was evaluated by measuring the plasma insulin levels and its hypoglycaemic effects after oral administration of the chitosan capsules containing insulin and additives. Little release of CF from the capsules was observed in an artificial gastric juice (pH 1), or in an artificial intestinal juice (pH 7). However, the release of CF was markedly increased in the presence of rat caecal contents. This group further evaluated colon-specific insulin delivery using chitosan capsules. It was found that these were stable in the stomach and small intestine but degraded by micro-organism in rat caecal contents upon entering into the colon proving their utility as carriers for colon targeted drug delivery of peptide and nonpeptide drugs.

Lorenzo-Lamosa et al. (Design of microencapsulated chitosan microspheres for colonic drug delivery. J Control Rel; 52: 109-118, 1998) prepared and demonstrated the efficacy of a system, which combines specific biodegradability and pH dependent release behavior. The system consists of chitosan microcores entrapped within acrylic microspheres containing diclofenac sodium as model drug. The drug was efficiently entrapped within the chitosan microcores using spray drying and then microencapsulated into Eudragit® L-100 and Eudragit® S-100 using an oil-in-oil solvent evaporation method. Release of the drug from chitosan multireservoir system was adjusted by changing the chitosan molecular weight or the type of chitosan salt. Furthermore, by coating the chitosan microcores with Eudragit®, perfect pH-dependent release profiles were attained.

In addition to the above cited melt extrusion polymers and plasticisers, the current invention also includes gelling agents such as gelatine, alginate, pectin and so forth, which are readily water soluble, and homogenously blended with the drug, meltable polymer and/or other excipients, including plasticisers. The homogenous minispheres thus, produced will be expected to demonstrate enhanced disintegration rates and possibly more rapid drug dissolution in the stomach, small intestine and colon.

In addition to the extrudate forming spherical or near-spherical forms due to the exertion of a vibrational force, the extrudate may also be formed by breaking the extrudate with a cutting tool, such as, but not limited to, a rotating knife.

EXAMPLES

Example 1

Single Layer Nimodipine Melt Extruded Seamless Sphere

An amount of nimodipine sufficient to provide an effective amount of the formulation may be mixed with a mixture of Eudragit® RS and RL. The weight ratio of nimodipine:Eudragit® polymer may vary from about 5:95% wt to 50:50% wt. The weight ratio of Eudragit® RS:Eudragit® RL may vary from about 0:100% wt to 100:0% wt. The solid mixture may then be placed in an extruder hopper or other mixer. The solid mixture is passed through the heated extruder at a temperature range of about 100° C. to about 160° C., as determined by the temperature setting of the extruder heating zone so that melting or softening of the RS or RL polymers occur. The entire nozzle may be subjected to an appropriate vibrational frequency. Upon exiting the nozzle, the solid spherical extrudate (Eudragit®/Nimodipine) may be cooled in air or in a cooling liquid, such as mineral oil.

| Ingredients | % w/w |
|---|---|
| Core Composition | |
| Nimodipine | 5-50 |
| Eudragit ® RS PO | 0-95 |
| Eudragit ® RL PO | 0-95 |

Example 2

Two-Layer Combination Proximal Diuretic (IR) and Distal Diuretic (SR)

An appropriate amount of a hydrochlorothiazide was mixed with gelucire 44/01 and Labrasol and heated to 65° C. The resulting solution may then be placed in an extruder for further mixing or extrusion to the extrusion nozzle at a suitable rate and temperature. The extrudate is passed through the inner nozzle inlet. Through an outer nozzle inlet is introduced a molten (~70° C.) mix of gelatine, acetazolamide and sorbitol. The entire nozzle may be subjected to an appropriate vibrational frequency. The resulting two-layer minicapsules are released into a cooling liquid to set. Once set, the minicapsules are centrifuged at a suitable force to remove any cooling oil residue.

| Ingredients | % w/w |
|---|---|
| Core Composition | |
| Hydrochlorothiazide | 2-50 |
| Gelucire 44/01 | 25-50 |
| Labrasol | 25-50 |
| Shell Composition | |
| Gelatin | 0-90 |
| Acetazolamide | 0-50 |
| Sorbitol | 0-10 |

Example 3

Single Layer Theophylline Sustained Release Melt Extruded Sphere

An appropriate amount of Theophylline, Acry-EZE, Carbopol 974P, Methocel K4M and Fumaric Acid is fed into an extruder hopper. The extruder to be used may have a double screw solids conveying mechanism that extends from the hopper through multiple heating zones to the extrusion nozzle, through the nozzle inlet. The solid mixture may then be passed through the heated extruder at a temperature range of about 75° C. to about 150° C., as determined by the temperature setting of the extruder heating zones so that melting of the polymers occurred, whereupon it exits the vibrating nozzle.

| Ingredients | % w/w |
|---|---|
| Core Composition | |
| Theophylline | 10-50 |
| Acryl-EZE | 30-80 |
| Triethyl Citrate | 0-20 |
| Carbopol 974P | 0-10 |
| Methocel K4M | 0-5 |
| Fumaric Acid | 0-5 |

Example 4

Single Layer Theophylline Sustained Release Melt Extruded Sphere

An appropriate amount of Theophylline and Carrageenan is mixed and fed into an extruder hopper. The extruder to be used may have a single or double screw conveying mechanism that extends from the hopper through multiple heating zones, to the extrusion nozzle, through the outer nozzle inlet. The solid mixture may then be passed through the heated extruder at a temperature range of about 75° C. to about 150° C., as determined by the temperature setting of the extruder heating zones so that melting of the polymers occurred, whereupon it exits the vibrating nozzle.

| Ingredients | % w/w |
|---|---|
| Core Composition | |
| Theophylline | 0-60 |
| Carrageenan | 0-60 |

Example 5

Single Layer Theophylline Sustained Release Melt Extruded Sphere

An appropriate amount of Theophylline, Chitosan, Gelatine and Sorbitol is mixed and fed into an extruder hopper. The extruder to be used may have a single or double screw conveying mechanism that extends from the hopper through multiple heating zones to the extrusion nozzle, through the outer nozzle inlet. The solid mixture may then be passed through the heated extruder at a temperature range of about 75° C. to about 150° C., as determined by the temperature setting of the extruder heating zones so that melting of the chitsoan and gelatine occurred, whereupon it exits the vibrating nozzle.

| Ingredients | % w/w |
|---|---|
| Core Composition | |
| Theophylline | 0-60 |
| Chitosan | 0-60 |
| Gelatin | 0-50 |
| Sorbitol | 0-20 |

Example 6

Two-Layer Heparin Extrudate (SR) in Gelatine Shell (with Mucoadhesive)

An appropriate amount of heparin, Witepsol H-15, Miglyol and lecithin is mixed and heated to ~70° C. and fed through an extruder to exit through the inner nozzle inlet of e di-centric nozzle. Through an outer nozzle inlet is introduced a molten (~70° C.) mix of gelatine, chitosan and sorbitol. The entire nozzle may be subjected to an appropriate vibrational frequency. The resulting two-layer minicapsules are released into a cooling liquid to set. Once set, the minicapsules are centrifuged at a suitable force to remove any cooling oil residue.

| Ingredients | % w/w |
|---|---|
| Core Composition | |
| Heparin | 25-50 |
| Witepsol H-15 | 25-50 |
| Miglyol | 0-20 |
| Lecithin | 0-20 |
| Shell Composition | |
| Chitosan | 0-90 |
| Gelatin | 0-50 |
| Sorbitol | 0-20 |

Example 7

Two-Layer Carvediol Extrudate (SR in Core)/Carvediol Extrudate (SR in Shell)

An appropriate amount of Carvediol, Witepsol H-15, Gelucire 44/01 is mixed and heated to ~70° C. and fed through an extruder to exit through the inner nozzle inlet of a di-centric nozzle. An appropriate amount of Eudragit® RL and RS, Gelatine, Carvediol (micronised) and Glycerol Monosterate is placed in a mixer and stirred for about 10 minutes. The solid mixture may then be placed in a second extruder hopper. The extruder to be used may have a double screw solids conveying mechanism that extends from the hopper through multiple heating zones to the extrusion nozzle, through the outer nozzle inlet. The solid mixture may then be passed through the heated extruder at a temperature range of about 75° C. to about 150° C., as determined by the temperature setting of the extruder heating zones so that melting of the Eudragit® occurred. Upon exiting the vibrating nozzle, the extrudate applies an even coat to the non-solid extrudate passing though the inner nozzle.

| Ingredients | % w/w |
|---|---|
| Core Composition | |
| Carvediol | 5-25 |
| Witepsol H-15 | 25-50 |
| Gelucire | 0-20 |
| Shell Composition | |
| Carvediol | 0-30 |
| Eudragit ® PL PO | 0-90 |
| Eudragit ® PS PO | 0-90 |
| Gelatine | 0-90 |
| Glycerol Monostearate | 0-20 |

Example 8

Two-Layer Hydralazine Extrudate (SR in Core)/Carvediol Extrudate (SR in Shell)

An appropriate amount of Hydralazine, Witepsol H-15, Miglyol and lecithin is mixed and heated to ~70° C. and fed through an extruder to exit through the inner nozzle inlet of a di-centric nozzle. An appropriate amount of Eudragit® RL and RS, Gelatine, Carvediol (micronised) and Glycerol Monosterate is placed in a mixer and stirred for about 10 minutes. The solid mixture may then be placed in a second extruder hopper. The extruder to be used may have a double screw solids conveying mechanism that extends from the hopper through multiple heating zones to the extrusion nozzle, through the outer nozzle inlet. The solid mixture may then be passed through the heated extruder at a temperature range of about 75° C. to about 150° C., as determined by the temperature setting of the extruder heating zones so that melting of the Eudragit® occurred. Upon exiting the vibrating nozzle, the extrudate applies an even coat to the non-solid extrudate passing though the inner nozzle.

| Ingredients | % w/w |
|---|---|
| Core Composition | |
| Hydralazine | 5-25 |
| Witepsol H-15 | 25-50 |
| Gelucire 44/01 | 0-20 |
| Shell Composition | |
| Carvediol | 0-30 |
| Eudragit ® PL PO | 0-90 |
| Eudragit ® PS PO | 0-90 |
| Gelatine | 0-90 |
| Glycerol Monostearate | 0-20 |

Example 9

Two-Layer Nucleic Acid (SR in Core) in Extruded Shell (with Mucoadhesive)

An appropriate amount of a nucleic acid, Witepsol H-15, Miglyol and lecithin is mixed and heated to ~70° C. and fed through an extruder to exit through the inner nozzle inlet of e di-centric nozzle. An appropriate amount of Eudragit® RL and RS, Amylose and Glycerol Monosterate is placed in a mixer and stirred for about 10 minutes. The solid mixture may then be placed in a second extruder hopper. The extruder to be used may have a double screw solids conveying mechanism that extends from the hopper through multiple heating zones to the extrusion nozzle, through the outer nozzle inlet. The solid mixture may then be passed through the heated extruder at a temperature range of about 75° C. to about 150° C., as determined by the temperature setting of the extruder heating zones so that melting of the Eudragit® occurred. Upon exiting the vibrating nozzle, the extrudate applies an even coat to the non-solid extrudate passing though the inner nozzle.

| Ingredients | % w/w |
|---|---|
| Core Composition | |
| Nucleic Acid | 25-50 |
| Witepsol H-15 | 25-50 |
| Miglyol | 0-20 |
| Lecithin | 0-20 |
| Shell Composition | |
| Amylose | 0-60 |
| Eudragit ® PL PO | 0-50 |
| Eudragit ® PS PO | 0-50 |
| Glycerol Monostearate | 0-20 |

Example 10

Single Layer Melt Extruded Felodipine Sphere

An appropriate mix of Felodipine, Eudragit® E, Eudragit® NE, Gelatine and Sorbitol is fed through an extruder, heated to suitable temperature to melt the Eudragit® polymers. The molten mixture is then fed through a nozzle inlet which may be subjected to an appropriate vibrational frequency. The resulting single-layer minicapsules are released into a cooling liquid to set. Once set, the minicapsules are centrifuged at a suitable force to remove any cooling oil residue.

| Ingredients | % w/w |
|---|---|
| Core Composition | |
| Felodipine | 10-50 |
| Eudragit ® E | 25-50 |
| Eudragit ® NE | 25-50 |
| Gelatin | 0-50 |
| Sorbitol | 0-10 |

Example 11

Single Layer Melt Extruded Felodipine Sphere

An appropriate amount of Felodipine, Eudragit® E and Eudragit® NE is fed into an extruder hopper. The extruder to be used may have a double screw solids conveying mechanism that extends from the hopper through multiple heating zones to the extrusion nozzle, through the nozzle inlet. The solid mixture may then be passed through the heated extruder at a temperature range of about 75° C. to about 150° C., as determined by the temperature setting of the extruder heating zones so that melting of the polymers occurred, whereupon it exits the vibrating nozzle.

| Ingredients | % w/w |
|---|---|
| Core Composition | |
| Felodipine | 10-50 |
| Eudragit ® E | 25-50 |
| Eudragit ® NE | 25-50 |

Example 12

Single-Layer Indomethacin Sustained Release Sphere

An appropriate amount of indomethacin, Eudragit® RD100, Pluronic F68 and Triethyl Citrate is fed into an extruder hopper. The extruder to be used may have a double screw solids conveying mechanism that extends from the hopper through multiple heating zones to the extrusion nozzle, through the nozzle inlet. The solid mixture may then be passed through the heated extruder at a temperature range of about 75° C. to about 150° C., as determined by the temperature setting of the extruder heating zones so that melting of the polymers occurred, whereupon it exits the die and is exposed to a cutting tool, the rotation of which dictates the size of the melt-extruded particle.

| Ingredients | % w/w |
|---|---|
| Core Composition | |
| Indomethacin | 10-50 |
| Eudragit ® RD 100 | 25-80 |
| Pluronic F68 | 0-10 |
| Triethyl Citrate | 0-20 |

Example 13

Single-Layer Ibuprofen Sustained Release Sphere

An appropriate amount of Ibuprofen, Eudragit® RD100 and PVP is fed into an extruder hopper. The extruder to be used may have a double screw solids conveying mechanism that extends from the hopper through multiple heating zones to the extrusion nozzle, through the nozzle inlet. The solid mixture may then be passed through the heated extruder at a temperature range of about 75° C. to about 150° C., as determined by the temperature setting of the extruder heating zones so that melting of the polymers occurred, whereupon it exits the die and is exposed to a cutting tool, the rotation of which dictates the size of the melt-extruded particle.

| Ingredients | % w/w |
|---|---|
| Core Composition | |
| Ibuprofen | 10-50 |
| Eudragit ® RD 100 | 25-80 |
| PVP | 0-30 |

Example 14

Single-Layer Diltiazem Sustained Release Sphere

An appropriate amount of Diltiazem HCL, Eudragit® RS PO, and Triethyl Citrate is fed into an extruder hopper. The extruder to be used may have a double screw solids conveying mechanism that extends from the hopper through multiple heating zones to the extrusion nozzle, through the nozzle inlet. The solid mixture may then be passed through the heated extruder at a temperature range of about 75° C. to about 150° C., as determined by the temperature setting of the extruder heating zones so that melting of the Eudragit®RS PO occurred. Prior to exiting the die and while the Diltiazem/Eudragit/Triethly Citrate extrudate remains in the molten state, molten gelatine is fed through a further extruder inlet fed and mixed, whereupon it exits the vibrating nozzle.

| Ingredients | % w/w |
|---|---|
| Core Composition | |
| Diltiazem HCl | 10-50 |
| Eudragit ® RS PO | 25-80 |
| Triethyl Citrate | 0-20 |

Example 15

Two-Layer Sustained Release Colonic Nicotinic Acid Product

An appropriate amount of a Nicotinic acid, Witepsol H-15, Miglyol and lecithin is mixed and heated to ~70° C. and fed through an extruder to exit through the inner nozzle inlet of a di-centric nozzle. An appropriate amount of Eudragit® RL and RS, Amylose and Glycerol Monosterate is placed in a mixer and stirred for about 10 minutes. The solid mixture may then be placed in a second extruder hopper. The extruder to be used may have a double screw solids conveying mechanism that extends from the hopper through multiple heating zones to the extrusion nozzle, through the outer nozzle inlet. The solid mixture may then be passed through the heated extruder at a temperature range of about 75° C. to about 150° C., as determined by the temperature setting of the extruder heating zones so that melting of the Eudragit® occurred. Upon exiting the vibrating nozzle, the extrudate applies an even coat to the non-solid extrudate passing though the inner nozzle.

| Ingredients | % w/w |
|---|---|
| Core Composition | |
| Nicotinic Acid | 25-50 |
| Witepsol H-15 | 25-50 |
| Miglyol | 0-20 |
| Lecithin | 0-20 |
| Shell Composition | |
| Amylose | 0-60 |
| Eudragit ® PL PO | 0-50 |
| Eudragit ® PS PO | 0-50 |
| Glycerol Monostearate | 0-20 |

Example 16

Two-Layer Fentanyl Citrate Sustained Release Melt Extruded Capsule

An appropriate amount of fentanly citrate was mixed with gelucire 44/01, Labrasol and N-Methyl Pyrrolidine and heated to 65° C. The resulting solution may then be placed in an extruder for further mixing or extrusion to the extrusion nozzle at a suitable rate and temperature. The extrudate is passed through the inner nozzle inlet. An appropriate amount of Eudragit® RS and RL (variable ratio), Gelatine and PVP is placed in a mixer and stirred for about 10 minutes. The solid mixture may then be placed in a second extruder hopper. The extruder to be used may have a double screw solids conveying mechanism that extends from the hopper through multiple heating zones to the extrusion nozzle, through the outer nozzle inlet. The solid mixture may then be passed through the heated extruder at a temperature range of about 75° C. to about 150° C., as determined by the temperature setting of the extruder heating zones so that melting of the Eudragit® occurred. Upon exiting the vibrating nozzle, the extrudate applies an even coat to the non-solid extrudate passing though the inner nozzle.

| Ingredients | % w/w |
|---|---|
| Core Composition | |
| Fentanyl Citrate | 5-10 |
| Labrasol | 30-50 |
| Gelucire 44/01 | 25-50 |
| N-Methyl Pyrolidine (NMP) | 0-12.5 |
| Shell Composition | |
| Eudragit ® RS PO | 0-90 |
| Eudragit ® RL PO | 0-90 |
| Gelatine | 0-90 |
| PVP | 0-20 |

Example 17

Two-Layer Zolpidem Extrudate (SR in Core)/Zolpidem Extrudate (IR in Shell)

An appropriate amount of Zolidem, Metolose® SM and PVP is mixed and heated to ~130° C. and fed through an extruder to exit through the inner nozzle inlet of a di-centric nozzle. An appropriate amount of Zolpide, Metolose® SR 90SH and Glycerol Monostearate, Carvediol (micronised) and Glycerol Monosterate is fed through an extruder to exit through the outer nozzle inlet of a di-centric nozzle. The two extruders may have a double screw solids conveying mechanism that extends from the hopper through multiple heating zones to the extrusion nozzle, through the inner and outer nozzle inlets. The solid mixture may then be passed through the heated extruder at a temperature range of about 75° C. to about 150° C., as determined by the temperature setting of the extruder heating zones so that melting of the Metolose® occurred. Upon exiting the vibrating nozzle, the layered extrudate is formed by cutting.

| Ingredients | % w/w |
|---|---|
| Core Composition | |
| Zolpidem | 5-25 |
| Metolose ® SM | 25-50 |
| PVP | 0-20 |
| Shell Composition | |
| Zolpidem | 0-30 |
| Metolose ® SR 90SH | 0-90 |
| Glycerol Monostearate | 0-20 |

The invention is not limited to the embodiments hereinbefore described which may be varied in detail.

The invention claimed is:

1. An extrusion process comprising the steps of: extruding a material that is flowable when heated; introducing a gelling agent to the extrudate such that the gelling and non-gelling components of the resultant mix are mixed through one another to form a mixed extrudate and passing the mixed extrudate through a nozzle having a single outlet to shape the mixed extrudate into a plurality of minispheres or minicapsules and wherein the nozzle is an apparatus having more than one inlet port in communication with the nozzle outlet; and wherein:

the extrudate is delivered into a first inlet port of the apparatus and the gelling agent is introduced to the extrudate through a second inlet port of the apparatus prior to passing the mixed extrudate through the nozzle outlet; and wherein the gelling agent and the extrudate entering the first and second inlet ports are at different temperatures;

and wherein a vibrational force is applied to the nozzle as the extrudate is passed through the nozzle, the process further comprising cooling the minispheres or minicapsules in a cooling gas or a cooling liquid.

2. The process of claim 1 wherein the material that is flowable when heated contains a pharmaceutical together with non-therapeutic compounds.

3. The process of claim 2 wherein the non-therapeutic compound is a surfactant.

4. The process of claim 2 wherein the non-therapeutic compound is a fatty acid ester.

5. The process of claim 4, wherein the fatty acid ester is selected from a fatty acid glyceride or an acetylated fatty acid.

6. The process of claim 5 wherein the extrusion is conducted employing a liquid feed comprising an extrudable polymer and a therapeutic compound.

7. The process of claim 1 wherein the gelling agent is gelatin.

8. The process of claim 1 wherein the gelling agent is included in a composition, and the gelling agent-containing composition comprises one or more members selected from active ingredients and additional functional excipients.

9. The process of claim 8 wherein the active ingredient is selected from a pharmaceutical, a biopharmaceutical, and/or a nutritional supplement.

10. The process of claim 1 wherein the material that is flowable when heated comprises a product selected from a pharmaceutical, a biopharmaceutical, and/or a nutritional supplement.

11. The process of claim 10 wherein the product is an immunomodulating agent.

12. The process of claim 11 wherein the immunomodulating entity is a vaccine adjuvant, allergen, anti-allergenic entity or an inducer of oral tolerance.

13. The process of claim 10 wherein the product is a drug and the minicapsules are adapted for oral delivery of the drug to the colon.

14. The process of claim 13 wherein the minicapsules further deliver the drug to the terminal ileum and the ileocecal junction.

15. The process of claim 10 wherein the drug comprises a drug selected from antigens and peptide drugs.

16. The process of claim 1 wherein the material that is flowable when heated comprises a pharmaceutical compound and a meltable polymer with a melting temperature that is compatible with the heat sensitivity of the pharmaceutical compound.

17. The process of claim 1 wherein the minicapsules comprise an extrudable polymer selected from derivatised cellulose, poly(methacrylate) derivative, poly(ethylene-co-vinyl acetate), poly(ethylene), poly(vinyl acetate-co-methacrylic acid), epoxy resins and caprolactones, poly(ethylene oxide), poly(ethylene glycol), waxes, fats, or lipid-based excipients.

18. The process of claim 1 wherein the mixed extrudate passes through the nozzle having a single outlet to form under gravity a flow of consecutive droplets that are cooled in a liquid.

19. The process of claim 1 wherein the material that is flowable when heated comprises a poly(ethylene glycol).

20. The process of claim 1 wherein the material that is flowable when heated comprises a wax, fat or lipid-based excipient.

21. The process of claim 1 wherein the material that is flowable when heated comprises an active pharmaceutical compound and a surfactant.

22. The process of claim 1 wherein the material that is flowable when heated comprises a lipophilic material that is liquid, semi-solid or solid at ambient temperature.

23. The process of claim 1 which further comprises coating the minicapsules or minispheres.

24. The process of claim 1 wherein the extrusion is conducted employing a liquid feed wherein: the material that is flowable when heated comprises a lipid-based excipient; the material that is flowable when heated comprises a drug selected from peptide drugs; and the process further comprises coating the minicapsules.

25. The process of claim 1 wherein the extrusion is conducted employing a liquid feed wherein: the material that is flowable when heated comprises a wax; the material that is flowable when heated comprises a drug selected from antigens; and the process further comprises coating the minicapsules or minispheres.

26. The process of claim 1 wherein the extrusion is conducted employing a liquid feed comprising an extrudable polymer and a therapeutic compound.

27. The process of claim 1 wherein the process further comprises preparing a formulation designed for oral delivery by means of inclusion of multiple minicapsules or minispheres in a hard gelatin capsule or in a sachet.

28. the process of claim 1 wherein the gelling agent is included with other melt extrudable controlled release materials.

29. The process of claim 1 wherein the gelling agent is included without other melt extrudable controlled release materials.

30. The process of claim 1 wherein the cooled minicapsules are selected from:
   (i) minicapsules which have a gelling component, and a non-gelling component mixed through one another, the non-gelling component comprising a wax, fat or lipid-based excipient and a product selected from a pharmaceutical, a biopharmaceutical, and/or a nutritional supplement; and
   (ii) minicapsules which have a gelling component and a non-gelling component mixed through one another, the non-gelling component comprising a polyethylene glycol) and a product selected from a pharmaceutical, a biopharmaceutical, and/or a nutritional supplement.

31. The process of claim 1 wherein the process incorporates lipid nanoparticles.

32. The process of claim 1 wherein the minicapsules have a diameter of from 0.5 mm to 5.0 mm.

33. The process of claim 1 wherein the nozzle outlet consists of a single outlet orifice.

34. The process of claim 1 wherein the minicapsules or minispheres once cooled are solid or semi-solid.

35. The process of claim 1 wherein the material that is flowable when heated is a liquid at room temperature.

36. The process of claim 1 wherein the extrusion process is carried out at a temperature of from about 35° C. to about 160° C.

37. The process of claim 1 wherein the gelling agent is selected from gelatin, alginate or pectin.

38. The process of claim 1 wherein the second inlet port is more proximal to the nozzle outlet relative to the first inlet port.

* * * * *